US011789964B2

(12) United States Patent
Seng et al.

(10) Patent No.: US 11,789,964 B2
(45) Date of Patent: *Oct. 17, 2023

(54) LOAD PLAN GENERATION

(71) Applicant: Oracle International Corporation, Redwood Shores, CA (US)

(72) Inventors: Terrel Co Seng, San Bruno, CA (US); Saurabh Verma, Cupertino, CA (US); Peter Songwen Xu, Palo Alto, CA (US)

(73) Assignee: Oracle International Corporation, Redwood Shores, CA (US)

( * ) Notice: Subject to any disclaimer, the term of this patent is extended or adjusted under 35 U.S.C. 154(b) by 574 days.

This patent is subject to a terminal disclaimer.

(21) Appl. No.: 16/238,290

(22) Filed: Jan. 2, 2019

(65) Prior Publication Data
US 2019/0138532 A1 May 9, 2019

Related U.S. Application Data

(63) Continuation of application No. 14/194,472, filed on Feb. 28, 2014, now Pat. No. 10,206,770.
(Continued)

(51) Int. Cl.
*G06F 16/25* (2019.01)
*B29C 48/00* (2019.01)
(Continued)

(52) U.S. Cl.
CPC .......... *G06F 16/254* (2019.01); *A61F 2/0063* (2013.01); *A61L 27/18* (2013.01);
(Continued)

(58) Field of Classification Search
CPC ....... G06F 16/254; B29C 48/00; B29C 48/02; B29C 71/0072; A61F 2/0063;
(Continued)

(56) References Cited

U.S. PATENT DOCUMENTS 6,694,310 B1 2/2004 Yu et al.
8,887,132 B1 11/2014 Hunter
(Continued)

OTHER PUBLICATIONS

Final Office Action for U.S. Appl. No. 14/194,472 dated Oct. 10, 2017, 28 pages.
(Continued)

*Primary Examiner* — Hosain T Alam
*Assistant Examiner* — Saba Ahmed
(74) *Attorney, Agent, or Firm* — Kilpatrick Townsend & Stockton LLP

(57) ABSTRACT

Load Plan Generator (LPG) is a BIAPPS utility for generating ODI load plans based on desired subset of fact tables for loading BIAPPS Data Warehouse. The tool simplifies the configurations process by minimizing the manual steps and configurations and provides a guided list of configurations steps and checklists. The load plan components can include different sets of load plans that will be stitched together by the load plan generator to create one load plan for loading chosen fact groups in the warehouse sourcing from different transaction systems.

21 Claims, 22 Drawing Sheets

Related U.S. Application Data

(60) Provisional application No. 61/843,289, filed on Jul. 5, 2013.

(51) Int. Cl.

| | |
|---|---|
| *B29C 48/02* | (2019.01) |
| *A61F 2/00* | (2006.01) |
| *A61L 27/18* | (2006.01) |
| *A61L 27/48* | (2006.01) |
| *A61L 31/06* | (2006.01) |
| *B29C 71/00* | (2006.01) |
| *D01D 5/088* | (2006.01) |
| *D01D 5/098* | (2006.01) |
| *D01D 5/16* | (2006.01) |
| *D01F 6/62* | (2006.01) |
| *D01F 6/84* | (2006.01) |
| *D02G 3/02* | (2006.01) |
| *B29K 67/00* | (2006.01) |
| *B29L 31/00* | (2006.01) |

(52) U.S. Cl.
CPC .............. *A61L 27/48* (2013.01); *A61L 31/06* (2013.01); *B29C 48/00* (2019.02); *B29C 48/02* (2019.02); *B29C 71/0072* (2013.01); *D01D 5/088* (2013.01); *D01D 5/098* (2013.01); *D01D 5/16* (2013.01); *D01F 6/62* (2013.01); *D01F 6/625* (2013.01); *D01F 6/84* (2013.01); *D02G 3/02* (2013.01); *A61F 2002/0068* (2013.01); *B29K 2067/00* (2013.01); *B29L 2031/753* (2013.01); *Y10T 428/1362* (2015.01); *Y10T 428/1369* (2015.01); *Y10T 428/249922* (2015.04); *Y10T 442/10* (2015.04); *Y10T 442/183* (2015.04); *Y10T 442/184* (2015.04); *Y10T 442/2525* (2015.04)

(58) Field of Classification Search
CPC .. A61F 2002/0068; A61L 27/18; A61L 27/48; A61L 31/06; D01D 5/088; D01D 5/098; D01D 5/16; D01F 6/62; D01F 6/625; D01F 6/84; D02G 3/02; Y10T 428/1362; Y10T 428/1369; Y10T 428/249922; Y10T 442/10; Y10T 442/183; Y10T 442/184; Y10T 442/2525; B29K 2067/00; B29L 2031/753

USPC ........................................................ 707/601
See application file for complete search history.

(56) References Cited

U.S. PATENT DOCUMENTS

| | | | |
|---|---|---|---|
| 2002/0099563 A1* | 7/2002 | Adendorff | G06Q 10/067 705/348 |
| 2010/0280990 A1* | 11/2010 | Castellanos | G06F 16/283 707/602 |
| 2011/0295794 A1 | 12/2011 | Venkatasubramanian et al. | |
| 2011/0301977 A1 | 12/2011 | Belcher et al. | |
| 2012/0192151 A1 | 7/2012 | Parkes et al. | |
| 2012/0239612 A1 | 9/2012 | George et al. | |
| 2013/0173539 A1* | 7/2013 | Gilder | G06F 16/273 707/610 |
| 2014/0007136 A1 | 1/2014 | Bettin et al. | |
| 2014/0040182 A1* | 2/2014 | Gilder | G06F 16/256 707/602 |
| 2014/0222873 A1 | 8/2014 | Nakadai et al. | |
| 2014/0280545 A1 | 9/2014 | Wagner et al. | |
| 2014/0344211 A1 | 11/2014 | Allan et al. | |
| 2014/0344625 A1 | 11/2014 | Thatte et al. | |
| 2015/0012476 A1 | 1/2015 | Seng et al. | |
| 2018/0089262 A1* | 3/2018 | Bhattacharjee | G06F 16/24535 |

OTHER PUBLICATIONS

Non-Final Office Action U.S. Appl. No. 14/194,472 dated Dec. 23, 2016, 26 pages.
Non-Final Office Action U.S. Appl. No. 14/194,472 dated Jan. 25, 2018, 35 pages.
Notice of Allowance U.S. Appl. No. 14/194,472 dated Oct. 1, 2018, 7 pages.
Davenport, Robert, "ETL vs ELT A Subjective View," Data Academy, Jun. 2008, 12 pages.
"Oracle Data Integrator for Business Intelligence," Oracle Data Sheet, 2008, 6 pages.
Miquel et al., "Oracle Fusion Middleware: Getting Started with Oracle Data Integrator," Oracle, 11g Release 1 (11.1.1), E12641-02, Apr. 2011, 104 pages.
"Oracle Business Intelligence Applications 11.1.7.1 What's New," Oracle Data Sheet, Oracle Business Intelligence 11g, 2013, 7 pages.

* cited by examiner

Create Load Plan

1700

Enter Name and Description — Select Fact Groups

* Name: Load Plan Demo 1
Description: For LPG Demo
Load Plan Type: Source Extract and Load (SDE, SIL and PLP)
Source Instances: EBS 1510
- ☐ All
- ☑ EBS 1510
- ☐ Siebel 811

FIG. 17A

Create Load Plan

1700

Enter Name and Description — Select Fact Groups

* Name: Load Plan Demo 1
Description: For LPG Demo
Load Plan Type: Source Extract and Load (SDE, SIL and PLP)
Source Instances:
- Source Extract (SDE)
- Source Extract and Load (SDE, SIL and PLP)
- Warehouse Load (SIL and PLP)
- Domain-only Extract and Load (SDE and SIL)

LOAD PLAN GENERATION

CROSS REFERENCES TO RELATED APPLICATIONS

This Continuation application claims priority to U.S. Non-Provisional application Ser. No. 14/194,472, filed Feb. 28, 2014 entitled, "LOAD PLAN GENERATION," which claims priority to and the benefit of U.S. Provisional Patent Application No. 61/843,289, filed Jul. 5, 2013 entitled "LOAD PLAN GENERATION," the entire contents of which are incorporated herein by reference for all purposes.

BACKGROUND OF THE INVENTION

In today's increasingly fast-paced business environment, organizations need to use more specialized software applications. Additionally, organizations need to ensure the coexistence of these applications on heterogeneous hardware platforms and systems and guarantee the ability to share data between applications and systems.

Load plans orchestrate execution of tasks for loading of data from sources into data warehouses (such as used by BI applications). Traditionally, users create load plans where users manually specify all sources, fact tables, transformations, and orchestration of all tasks using various tools.

One problem with current automated load plan generation tools is that the tools require their own repositories holding information used to generate load plans and also require synchronization of those repositories with the actual tools that implement parts of the load plans.

Accordingly, what is desired is to solve problems relating to developing data integration scenarios, some of which may be discussed herein. Additionally, what is desired is to reduce drawbacks relating to developing data integration scenarios, some of which may be discussed herein.

BRIEF SUMMARY OF THE INVENTION

The following portion of this disclosure presents a simplified summary of one or more innovations, embodiments, and/or examples found within this disclosure for at least the purpose of providing a basic understanding of the subject matter. This summary does not attempt to provide an extensive overview of any particular embodiment or example. Additionally, this summary is not intended to identify key/critical elements of an embodiment or example or to delineate the scope of the subject matter of this disclosure. Accordingly, one purpose of this summary may be to present some innovations, embodiments, and/or examples found within this disclosure in a simplified form as a prelude to a more detailed description presented later.

In various embodiments, a load plan generation application is disclosed for orchestrating execution of packages for loading data from one or more sources into one or more data warehouses. The load plan generation can be based on load plan components that contain an end-to-end load of a data warehouse sourcing from all possible types of transaction systems. These components will not be used for actual loading of the warehouse but separate load plan will be generated therefrom for each execution plan defined by users. The generated load plan may only contain steps required to load the data warehouse for the selected list of fact groups in the execution plan.

A method for generating load plans used to load data from data sources into data warehouses is disclosed that includes receiving, at one or more computer systems, one or more data source definitions each specifying one or more data sources from which to load data into a data warehouse. Information is received indicative of one or more phases for loading data between data sources and data warehouses. For each data source definition in the one or more data source definitions, a determination is made how to configure the one or more phases with one or more of a plurality of predefined load plan components based on the one or more data sources of the data source definition satisfying one or more design dependencies. Each of the plurality of predefined load plan components specifying one or more tasks indicative of how data is loaded between a data source and a data warehouse. Additionally, a determination is made how to configure the one or more of the plurality of predefined load plan components based on satisfying one or more runtime dependencies between the one or more tasks in the one or more of the plurality of predefined load plan components. A load plan is then generated based on the configured one or more phases and the configured one or more of a plurality of load plan components.

In one aspect, determining how to configure the one or more phases with the one or more of the plurality of predefined load plan components comprises determining one or more fact groups associated with the one or more data sources of the data source definition. One or more dimensions are determined based on dimension dependencies for the determined fact groups associated with the one or more data sources of the data source definition. Staging information is determined associated with the determined fact groups and the determined dimensions.

In another aspect, determining how to configure the one or more of the plurality of predefined load plan components comprises determining intermediate sources used in the one or more tasks of each of the one or more of the plurality of predefined load plan components. One or more of the one or more tasks of each of the one or more of the plurality of predefined load plan components are configured based on the intermediate sources.

Configuring at least one of the plurality of load plan components may be done based on a set of load plan rules. At least one rule may configure a design time dependency or a runtime dependency based on one or more fact tables belonging to one or more fact groups. At least one rule may configure a design time dependency or a runtime dependency based on one or more dimension dependencies to one or more fact groups. At least one rule may configure a design time dependency or a runtime dependency based on staging tables related to fact groups or dimensions. At least one rule may configure a design time dependency or a runtime dependency based on one or more source tables required to support a fact group or dimension. Finally, at least one rule may configure a design time dependency or a runtime dependency based on one or more keywords associating tables to fact groups or dimensions.

A non-transitory computer-readable medium in one embodiment stores computer-executable code for generating load plans used to load data from data sources into data warehouses. The non-transitory computer-readable medium includes code for receiving one or more data source definitions each specifying one or more data sources from which to load data into a data warehouse; code for receiving information indicative of one or more phases for loading data between data sources and data warehouses; and code for, for each data source definition in the one or more data source definitions: determining how to configure the one or more phases with one or more of a plurality of predefined load plan components based on the one or more data sources of the data source definition satisfying one or more design dependencies, each of the plurality of predefined load plan components specifying one or more tasks indicative of how data is loaded between a data source and a data warehouse, and determining how to configure the one or more of the plurality of predefined load plan components based on satisfying one or more runtime dependencies between the one or more tasks in the one or more of the plurality of predefined load plan components; and code for generating a load plan based on the configured one or more phases and the configured one or more of a plurality of load plan components.

A system in one embodiment for generating load plans used to load data from data sources into data warehouses includes a hardware processor; and a non-transitory memory storing a set of instructions which when executed by the processor configure the processor to: receive one or more data source definitions each specifying one or more data sources from which to load data into a data warehouse; receive information indicative of one or more phases for loading data between data sources and data warehouses; and for each data source definition in the one or more data source definitions: determine how to configure the one or more phases with one or more of a plurality of predefined load plan components based on the one or more data sources of the data source definition satisfying one or more design dependencies, each of the plurality of predefined load plan components specifying one or more tasks indicative of how data is loaded between a data source and a data warehouse, and determine how to configure the one or more of the plurality of predefined load plan components based on satisfying one or more runtime dependencies between the one or more tasks in the one or more of the plurality of predefined load plan components; and generate a load plan based on the configured one or more phases and the configured one or more of a plurality of load plan components.

A further understanding of the nature of and equivalents to the subject matter of this disclosure (as well as any inherent or express advantages and improvements provided) should be realized in addition to the above section by reference to the remaining portions of this disclosure, any accompanying drawings, and the claims.

BRIEF DESCRIPTION OF THE DRAWINGS

In order to reasonably describe and illustrate those innovations, embodiments, and/or examples found within this disclosure, reference may be made to one or more accompanying drawings. The additional details or examples used to describe the one or more accompanying drawings should not be considered as limitations to the scope of any of the claimed inventions, any of the presently described embodiments and/or examples, or the presently understood best mode of any innovations presented within this disclosure.

FIGS. 17A and 17B are screenshots of a user interface configured to allow users to create load plan definitions in one embodiment according to the present invention.

FIG. 18 is a screenshot of a user interface configured to allow users to specify fact groups for load plan definitions.

DETAILED DESCRIPTION OF THE INVENTION

Load Plan Generator (LPG) is a BIAPPS utility for generating ODI load plans based on desired subset of fact tables for loading BIAPPS Data Warehouse. This disclosure relates to tools and techniques that simplify the configurations process by minimizing the manual steps needed to orchestrate execution of tasks for loading of data from sources into data warehouses. In one aspect, a load plan designer is provided with a guided list of configurations steps and checklists to build a set of load plan components. The load plan components include different sets of load plans and can be stitched together by a load plan generator to create one or more load plans for loading chosen fact groups in the data warehouse sourcing from different transaction systems.

Introduction

In various embodiments, a data integration system enables users to create a logical design which is platform and technology independent. The user can create a logical design that defines, at a high level, how a user wants data to flow between sources and targets. The tool can analyze the logical design, in view of the user's infrastructure, and create a physical design. The logical design can include a plurality of components corresponding to each source and target in the design, as well as operations such as joins or filters, and access points. Each component when transferred to the physical design generates code to perform operations on the data. Depending on the underlying technology (e.g., SQL Server, Oracle, Hadoop, etc.) and the language used (SQL, pig, etc.) the code generated by each component may be different.

In one aspect, a user of data integration system is not required to specify all data attributes at each component in the logical design, from start to end. The data integration system provides a plurality of component types, such as projector and selector types, that avoid the need to fully declare the information that flows through the logical design. The data integration system is able to decide what attributes are needed at operations represented by predetermined component types. This simplifies both the design and maintenance.

Figure 1:
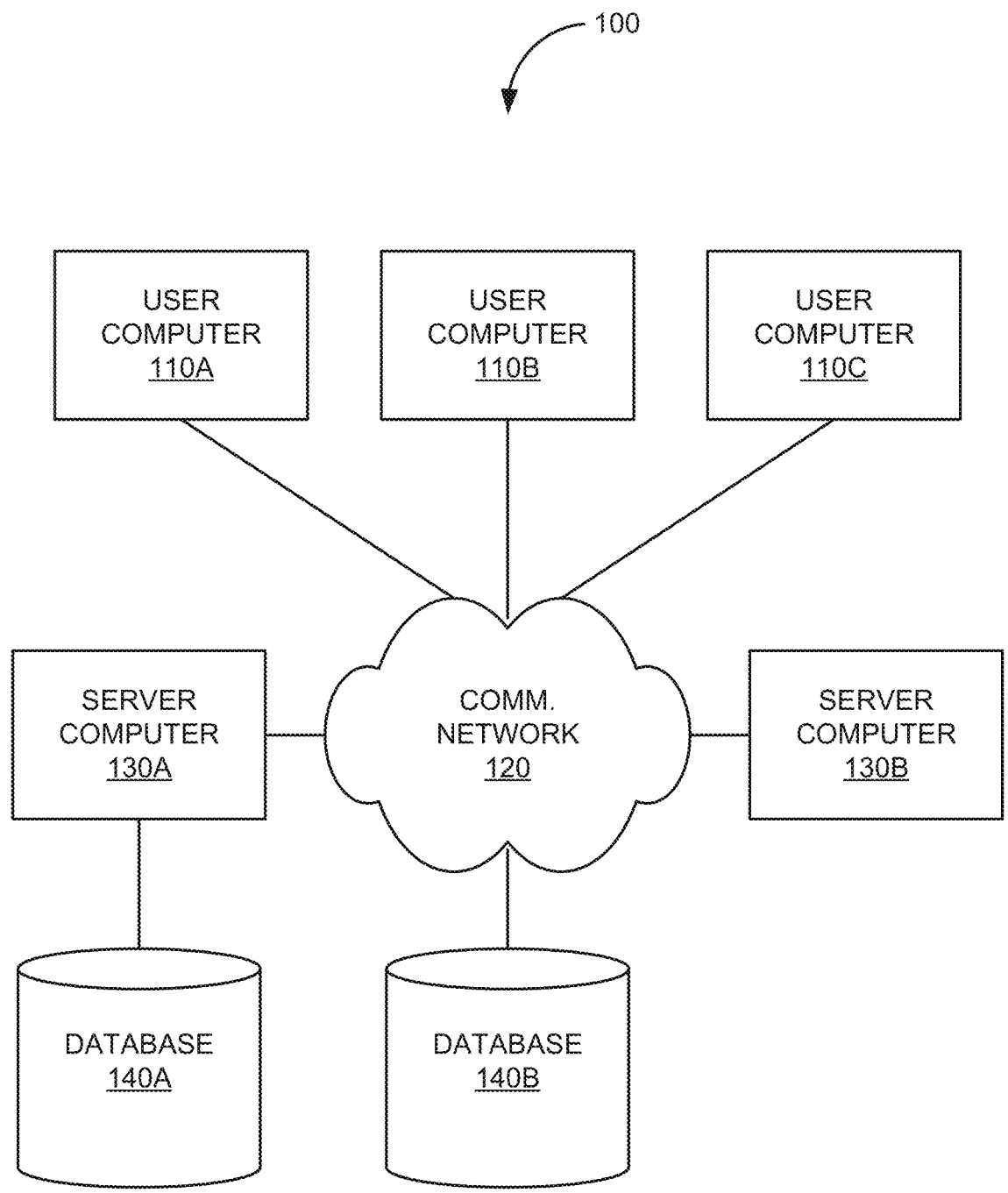
FIG. 1 is a simplified illustration of a system that may incorporate an embodiment of the present invention.

FIG. 1 is a simplified illustration of system 100 that may incorporate an embodiment or be incorporated into an embodiment of any of the innovations, embodiments, and/or examples found within this disclosure. FIG. 1 is merely illustrative of an embodiment incorporating the present invention and does not limit the scope of the invention as recited in the claims. One of ordinary skill in the art would recognize other variations, modifications, and alternatives.

In one embodiment, system 100 includes one or more user computers 110 (e.g., computers 110A, 110B, and 110C). User computers 110 can be general purpose personal computers (including, merely by way of example, personal computers and/or laptop computers running any appropriate flavor of Microsoft Corp.'s Windows™ and/or Apple Corp.'s Macintosh™ operating systems) and/or workstation computers running any of a variety of commercially-available UNIX™ or UNIX-like operating systems. These user computers 110 can also have any of a variety of applications, including one or more applications configured to perform methods of the invention, as well as one or more office applications, database client and/or server applications, and web browser applications.

Alternatively, user computers 110 can be any other electronic device, such as a thin-client computer, Internet-enabled mobile telephone, and/or personal digital assistant, capable of communicating via a network (e.g., communications network 120 described below) and/or displaying and navigating web pages or other types of electronic documents. Although the exemplary system 100 is shown with three user computers, any number of user computers or devices can be supported.

Certain embodiments of the invention operate in a networked environment, which can include communications network 120. Communications network 120 can be any type of network familiar to those skilled in the art that can support data communications using any of a variety of commercially-available protocols, including without limitation TCP/IP, SNA, IPX, AppleTalk, and the like. Merely by way of example, communications network 120 can be a local area network ("LAN"), including without limitation an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network, including without limitation a network operating under any of the IEEE 802.11 suite of protocols, the Bluetooth™ protocol known in the art, and/or any other wireless protocol; and/or any combination of these and/or other networks.

Embodiments of the invention can include one or more server computers 130 (e.g., computers 130A and 130B). Each of server computers 130 may be configured with an operating system including without limitation any of those discussed above, as well as any commercially-available server operating systems. Each of server computers 130 may also be running one or more applications, which can be configured to provide services to one or more clients (e.g., user computers 110) and/or other servers (e.g., server computers 130).

Merely by way of example, one of server computers 130 may be a web server, which can be used, merely by way of example, to process requests for web pages or other electronic documents from user computers 110. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 110 to perform methods of the invention.

Server computers 130, in some embodiments, might include one or more file and or/application servers, which can include one or more applications accessible by a client running on one or more of user computers 110 and/or other server computers 130. Merely by way of example, one or more of server computers 130 can be one or more general purpose computers capable of executing programs or scripts in response to user computers 110 and/or other server computers 130, including without limitation web applications (which might, in some cases, be configured to perform methods of the invention).

Merely by way of example, a web application can be implemented as one or more scripts or programs written in any programming language, such as Java, C, or C++, and/or any scripting language, such as Perl, Python, or TCL, as well as combinations of any programming/scripting languages. The application server(s) can also include database servers, including without limitation those commercially available from Oracle, Microsoft, IBM and the like, which can process requests from database clients running on one of user computers 110 and/or another of server computers 130.

In some embodiments, an application server can create web pages dynamically for displaying the information in accordance with embodiments of the invention. Data provided by an application server may be formatted as web pages (comprising HTML, XML, Javascript, AJAX, etc., for example) and/or may be forwarded to one of user computers 110 via a web server (as described above, for example). Similarly, a web server might receive web page requests and/or input data from one of user computers 110 and/or forward the web page requests and/or input data to an application server.

In accordance with further embodiments, one or more of server computers 130 can function as a file server and/or can include one or more of the files necessary to implement methods of the invention incorporated by an application running on one of user computers 110 and/or another of server computers 130. Alternatively, as those skilled in the art will appreciate, a file server can include all necessary files, allowing such an application to be invoked remotely by one or more of user computers 110 and/or server computers 130. It should be noted that the functions described with respect to various servers herein (e.g., application server, database server, web server, file server, etc.) can be performed by a single server and/or a plurality of specialized servers, depending on implementation-specific needs and parameters.

In certain embodiments, system 100 can include one or more databases 140 (e.g., databases 140A and 140B). The location of the database(s) 140 is discretionary: merely by way of example, database 140A might reside on a storage medium local to (and/or resident in) server computer 130A (and/or one or more of user computers 110). Alternatively, database 140B can be remote from any or all of user computers 110 and server computers 130, so long as it can be in communication (e.g., via communications network 120) with one or more of these. In a particular set of embodiments, databases 140 can reside in a storage-area network ("SAN") familiar to those skilled in the art. (Likewise, any necessary files for performing the functions attributed to user computers 110 and server computers 130 can be stored locally on the respective computer and/or remotely, as appropriate). In one set of embodiments, one or more of databases 140 can be a relational database that is adapted to store, update, and retrieve data in response to SQL-formatted commands. Databases 140 might be controlled and/or maintained by a database server, as described above, for example.

Data Integration Overview

Figure 2:
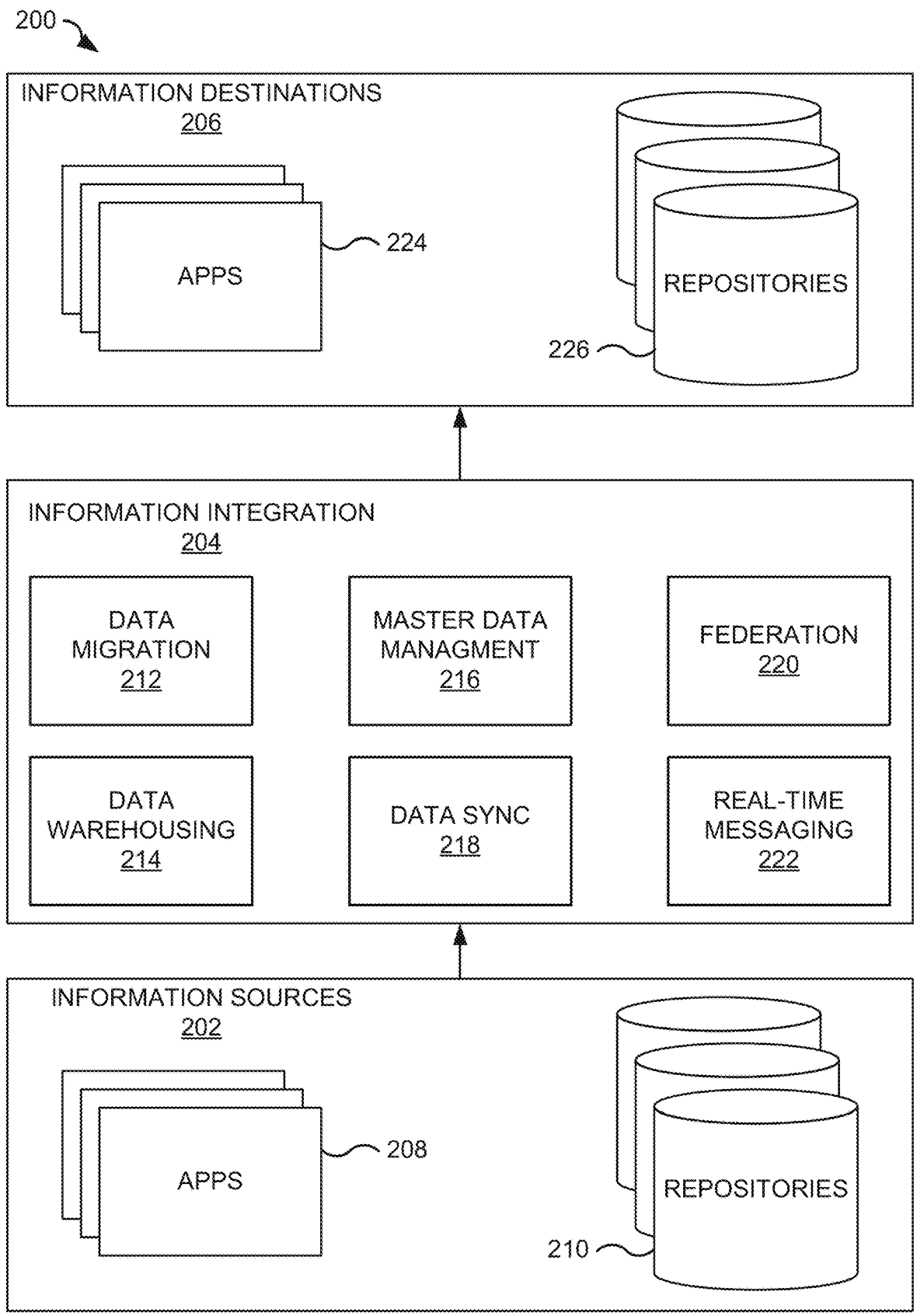
FIG. 2 is a block diagram of a data integration system according to an embodiment of the present invention.

FIG. 2 is a simplified block diagram of data integration system 200 according to an embodiment of the present invention. FIG. 2 is a simplified illustration of data integration system 200 that may incorporate various embodiments or implementations of the one or more inventions presented within this disclosure. FIG. 2 is merely illustrative of an embodiment or implementation of an invention disclosed herein should not limit the scope of any invention as recited in the claims. One of ordinary skill in the art may recognize through this disclosure and the teachings presented herein other variations, modifications, and/or alternatives to those embodiments or implementations illustrated in the figures.

In this embodiment, data integration system 200 includes information sources 202, information integration 204, and information destinations 206. In general, information flows from information sources 202 to information integration 204 whereby the information may be consumed, made available, or otherwise used by information destinations 206. Data flows may be unidirectional or bidirectional. In some embodiments, one or more data flows may be present in data integration system 200.

Information sources 202 are representative of one or more hardware and/or software elements configured to source data. Information sources 202 may provide direct or indirect access to the data. In this embodiment, information sources 202 include one or more applications 208 and one or more repositories 210.

Applications 208 are representative of traditional applications, such as desktop, hosted, web-based, or cloud-based applications. Applications 208 may be configured to receive, process, and maintain data for one or more predetermined purposes. Some examples of applications 208 include customer relationship management (CRM) applications, financial services applications, government and risk compliance applications, human capital management (HCM), procurement applications, supply chain management applications, project or portfolio management applications, or the like. Applications 208 may include functionality configured for manipulating and exporting application data in a variety of human-readable and machine-readable formats, as is known in the art. Applications 208 may further access and store data in repositories 210.

Repositories 210 are representative of hardware and/or software elements configured to provide access to data. Repositories 210 may provide logical and/or physical partitioning of data. Repositories 210 may further provide for reporting and data analysis. Some examples of repositories 210 include databases, data warehouses, cloud storage, or the like. A repository may include a central repository created by integrating data from one or more applications 208. Data stored in repositories 210 may be uploaded from an operational system. The data may pass through additional operations before being made available in a source.

Information integration 204 is representative of one or more hardware and/or software elements configured to provide data integration services. Direct or indirect data integration services can be provided in information integration 204. In this embodiment, information integration 204 includes data migration 212, data warehousing 214, master data management 216, data synchronization 218, federation 220, and real-time messaging 222. It will be understood that information integration 204 can include one or more modules, services, or other additional elements than those shown in here that provide data integration functionality.

Data migration 212 is representative of one or more hardware and/or software elements configured to provide data migration. In general, data migration 212 provides one or more processes for transferring data between storage types, formats, or systems. Data migration 212 usually provides for manual or programmatic options to achieve a migration. In a data migration procedure, data on or provided by one system is mapped to another system providing a design for data extraction and data loading. A data migration may involve one or more phases, such a design phase where one or more designs are created that relate data formats of a first system to formats and requirements of a second system, a data extraction phase where data is read from the first system, a data cleansing phase, and a data loading phase where data is written to the second system. In some embodiments, a data migration may include a data verification phases to determine whether data is accurately processed in any of the above phases.

Data warehousing 214 is representative of one or more hardware and/or software elements configured to provide databases used for reporting and data analysis. A data warehouse is typically viewed as a central repository of data which is created by integrating data from one or more disparate sources. Data warehousing 214 may include the current storage of data as well as storage of historical data. Data warehousing 214 may include typical extract, transform, load (ETL)-based data warehouse whereby staging, data integration, and access layers house key functions. In one example, a staging layer or staging database stores raw data extracted from each of one or more disparate source data systems. An integration layer integrates disparate data sets by transforming the data from the staging layer often storing this transformed data in an operational data store (ODS) database. The integrated data is then moved to yet another database, often called the data warehouse database. The data can be arranged into hierarchical groups (often called dimensions) and into facts and aggregate facts. An access layer may be provided to help users or other systems retrieve data. Data warehouses can be subdivided into data marts whereby each data mart stores subsets of data from a warehouse. In some embodiments, data warehousing 214 may include business intelligence tools, tools to extract, transform and load data into the repository, and tools to manage and retrieve metadata.

Master data management 216 is representative of one or more hardware and/or software elements configured to manage a master copy of data. Master data management 216 may include a set of processes, governance, policies, standards and tools that consistently define and manage master data. Master data management 216 may include functionality for removing duplicates, standardizing data, and incorporating rules to eliminate incorrect data from entering a system in order to create an authoritative source of master data. Master data management 216 may provide processes for collecting, aggregating, matching, consolidating, quality-assuring, persisting and distributing data throughout an organization to ensure consistency and control in the ongoing maintenance and application use of information.

Data synchronization 218 is representative of one or more hardware and/or software elements configured to synchronize data. Data synchronization 218 may provide for establishing consistency among data from a source to a target and vice versa. Data synchronization 218 may further provide for the continuous harmonization of the data over time.

Federation 220 is representative of one or more hardware and/or software elements configured to consolidate a view of data from constituent sources. Federation 220 may transparently map multiple autonomous database systems into a single federated database. The constituent databases maybe interconnected via a computer network and may be geographically decentralized. Federation 220 provides an alternative to merging several disparate databases. A federated database, or virtual database, for example, may provide a composite of all constituent databases. Federation 220 may not provide actual data integration in the constituent disparate databases but only in the view.

Federation 220 may include functionality that provides a uniform user interface, enabling users and clients to store and retrieve data in multiple noncontiguous databases with a single query—even if the constituent databases are heterogeneous. Federation 220 may include functionality to decompose a query into subqueries for submission to relevant constituent data sources and composite the result sets of the subqueries. Federation 220 can include one or more wrappers to the subqueries to translate them into appropriate query languages. In some embodiments, federation 220 is a collection of autonomous components that make their data available to other members of the federation through the publication of an export schema and access operations.

Real-time messaging 222 is representative of one or more hardware and/or software elements configured to provide messaging services subject to a real-time constraint (e.g., operational deadlines from event to system response). Real-time messaging 222 may include functionality that guarantees an action or response within strict time constraints. In one example, real-time messaging 222 may be tasked with taking some orders and customer data from one database, combining it with some employee data held in a file, and then loading the integrated data into a Microsoft SQL Server 2000 database. Because orders need to be analyzed as they arrive, real-time messaging 222 may pass the orders through to a target database in as close to real time as possible and extract only the new and changed data to keep the workload as small as possible.

Information destinations 206 are representative of one or more hardware and/or software elements configured to store or consume data. In this embodiment, information destinations 206 may provide direct or indirect access to the data. In this embodiment, information destinations 206 include one or more applications 224 and one or more repositories 226.

Applications 224 are representative of traditional applications, such as desktop, hosted, web-based, or cloud-based applications. Applications 224 may be configured to receive, process, and maintain data for one or more predetermined purposes. Some examples of applications 224 include customer relationship management (CRM) applications, financial services applications, government and risk compliance applications, human capital management (HCM), procurement applications, supply chain management applications, project or portfolio management applications, or the like. Applications 224 may include functionality configured for manipulating and importing application data in a variety of human-readable and machine-readable formats, as is known in the art. Applications 224 may further access and store data in repositories 226.

Repositories 226 are representative of hardware and/or software elements configured to provide access to data. Repositories 226 may provide logical and/or physical partitioning of data. Repositories 226 may further provide for reporting and data analysis. Some examples of repositories 226 include databases, data warehouses, cloud storage, or the like. A repository may include a central repository created by integrating data from one or more applications 226. Data stored in repositories 226 may be uploaded or imported through information integration 204. The data may pass through additional operations before being made available at a destination.

Data Integration System

Figure 3:
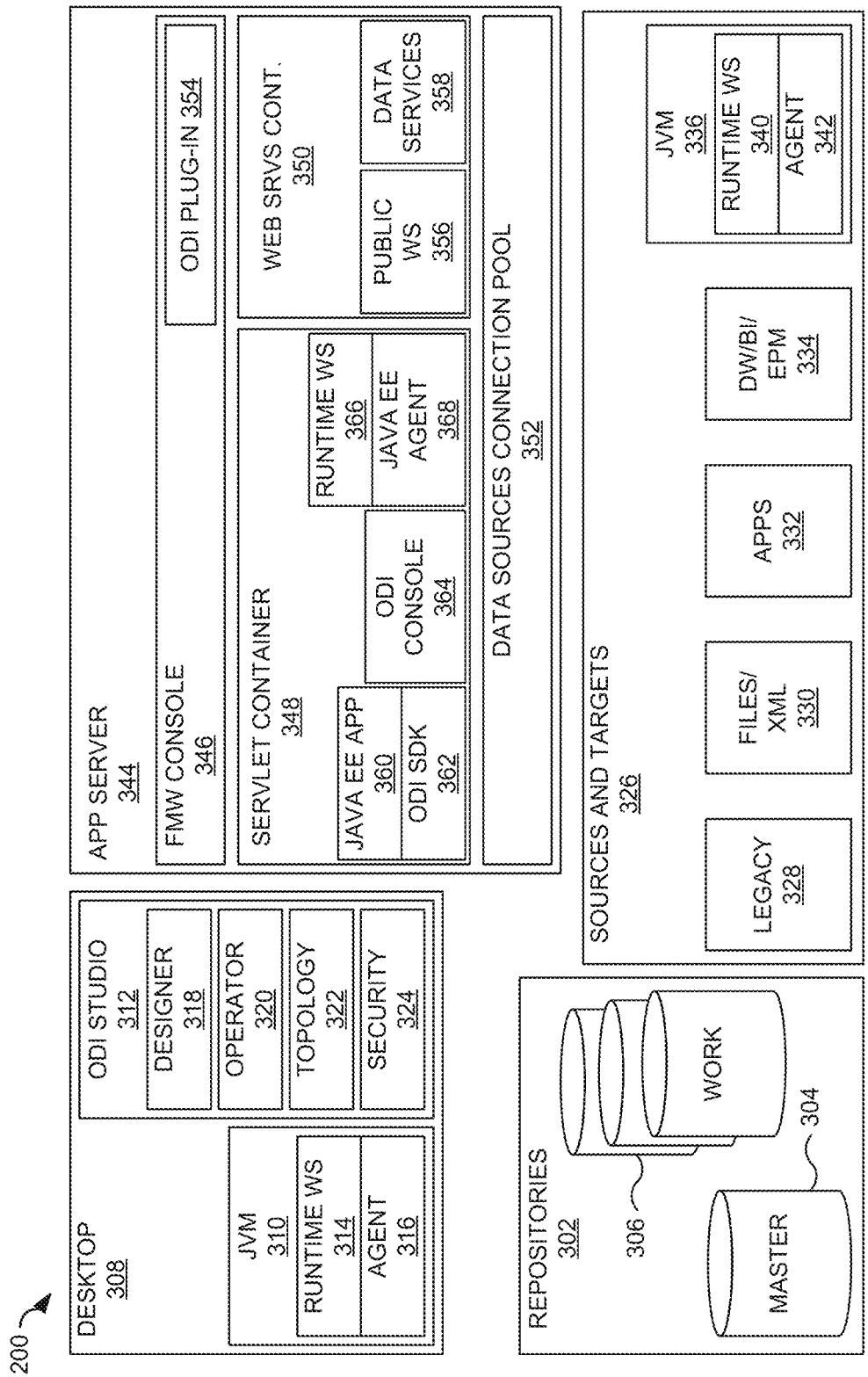
FIG. 3 is a simplified block diagram of a hardware/software stack that may be used to implement a data integration system according to an embodiment of the present invention.

FIG. 3 is a simplified block diagram of a hardware/software stack that may be used to implement data integration system 200 according to an embodiment of the present invention. FIG. 3 is merely illustrative of an embodiment or implementation of an invention disclosed herein should not limit the scope of any invention as recited in the claims. One of ordinary skill in the art may recognize through this disclosure and the teachings presented herein other variations, modifications, and/or alternatives to those embodiments or implementations illustrated in the figures. One example of components found within data integration system 200 according to this embodiment may include ORACLE DATA INTEGRATOR, a member of the ORACLE FUSION Middleware family of products provided by Oracle of Redwood Shores, Calif. ORACLE DATA INTEGRATOR is a Java-based application that uses one or more databases to perform set-based data integration tasks. In addition, ORACLE DATA INTEGRATOR can extract data, provide transformed data through Web services and messages, and create integration processes that respond to and create events in service-oriented architectures. ORACLE DATA INTEGRATOR is based on an ELT [extract-Load and Transform] architecture rather than conventional ETL [extract-transform-load] architectures. A copy of a user manual for ORACLE DATA INTEGRATOR is attached to this disclosure and incorporated herein by reference for all purposes.

In various embodiments, data integration system 200 provides a new declarative design approach to defining data transformation and integration processes, resulting in faster and simpler development and maintenance. Data integration system 200 thus separates declarative rules from the implementation details. Data integration system 200 further provides a unique E-LT architecture (Extract-Load Transform) for the execution of data transformation and validation processes. This architecture in embodiments eliminates the need for a standalone ETL server and proprietary engine. In some embodiments, data integration system 200 instead leverages the inherent power of RDBMS engines.

In some embodiments, data integration system 200 integrates in one or more middleware software packages, such as the ORACLE FUSION MIDDLEWARE platform and becomes a component of the middleware stack. As depicted in FIG. 3 data integration system 200 may provide run-time components as Java EE applications.

In this example, one component of data integration system 200 is repositories 302. Repositories 302 are representative of hardware and/or software elements configured to store configuration information about an IT infrastructure, metadata of all applications, projects, scenarios, and execution logs. In some aspects, multiple instances of repositories 302 can coexist in an IT infrastructure, for example Development, QA, User, Acceptance, and Production. Repositories 302 are configured to allow several separated environments that exchange metadata and scenarios (for example: Development, Test, Maintenance and Production environments). Repositories 302 further are configured to act as a version control system where objects are archived and assigned a version number.

In this example, repositories 302 is composed of at least one master repository 304 and one or more work repositories 306. Objects developed or configured for use within data integration system 200 may be stored in one of these repository types. In general, master repository 304 stores the following information: security information including users, profiles and rights, topology information including technologies, server definitions, schemas, contexts, languages and so forth, and versioned and archived objects. The one or more work repositories 306 may contain actual developed objects.

Several work repositories may coexist in data integration system 200 (for example, to have separate environments or to match a particular versioning life cycle). The one or more work repositories 306 store information for models, including schema definition, data stores structures and metadata, fields and columns definitions, data quality constraints, cross references, data lineage, and so forth. The one or more work repositories 306 may further store projects, including business rules, packages, procedures, folders, knowledge modules, variables and so forth, and scenario execution, including scenarios, scheduling information and logs. In some aspects, the one or more work repositories 306 may contain only execution information (typically for production purposes), and be designated as an execution repository.

In various embodiments, repositories 302 store one or more ETL projects. An ETL project defines or otherwise specifies one or more data models that model data attributes of data in a source or target. An ETL project further provides for data quality control as well as defining mappings to move and transform data. Data integrity control ensures the overall consistency of the data. Application data is not always valid for the constraints and declarative rules imposed by a particular source or target. For example, orders may be found with no customer, or order lines with no product, and so forth. Data integration system 200 provides a working environment to detect these constraint violations and to store them for recycling or reporting purposes.

In some embodiments of data integration system 200, there are two different types of controls: Static Control and Flow Control. Static Control implies the existence of rules that are used to verify the integrity of application data. Some of these rules (referred to as constraints) may already be implemented in data servers (using primary keys, reference constraints, etc.) Data integration system 200 allows for the definition and checking of additional constraints, without declaring them directly in a source. Flow Control relates to targets of transformation and integration processes that implement their own declarative rules. Flow Control verifies an application's incoming data according to these constraints before loading the data into a target. Flow control procedures are general referred to as mappings.

An ETL project can be automated into a package that can be deployed for execution in a runtime environment. Accordingly, the automation of data integration flows is achieved by sequencing the execution of the different steps (mappings, procedures, and so forth) in a package and by producing a production scenario containing ready-to-use code for each of these steps. A package is typically made up of a sequence of steps organized into an execution diagram. Packages are the main objects used to generate scenarios for production. They represent the data integration workflow and can perform jobs, such as for example: start a reverse-engineering process on a datastore or a model, send an email to an administrator, download a file and unzip it, define the order in which mappings must be executed, and define loops to iterate over execution commands with changing parameters.

A scenario is designed to put a source component (mapping, package, procedure, variable) into production. A scenario results from the generation of code (SQL, shell, and so forth) for this component. Once generated, the code of the source component is frozen and the scenario is stored inside repositories 302, such as one or more of work repositories 306. A scenario can be exported and then imported into different production environments.

In various embodiments, data integration system 200 is organized around repositories 302 in a modular fashion accessed by Java graphical modules and scheduling agents. Graphical modules can be used to design and build one or more integration processes stored in repositories 302. Administrators, Developers and Operators may use a development studio to access repositories 302. Agents can be used to schedule and coordinate a set of integration tasks associated with an integration process stored in repositories 302. For example, at runtime, an agent deployed on a desktop, web services, or otherwise in communication with a source coordinates the execution of one or more integration processes. The agent may retrieve code stored in master repository 304, connect to various source and target systems, and orchestrate an overall data integration process or scenario.

In this embodiment, data integration system 200 includes desktop 308 that may include one or more of the above discussed graphical modules and/or agents. Desktop 308 is representative of one or more desktop or workstation computing devices, such as personal computers, laptops, netbooks, tablets, and the like. Desktop 308 includes a Java virtual machine (JVM) 310 and Oracle Data Integrator (ODI) Studio 312. Java virtual machine (JVM) 310 is a virtual machine that can execute Java bytecode. JVM 310 is most often implemented to run on an existing operating system, but can also be implemented to run directly on hardware. JVM 310 provides a run-time environment in which Java bytecode can be executed, enabling features such as runtime web service (WS) 314 and agent 316. JVM 310 may include a Java Class Library, a set of standard class libraries (in Java bytecode) that implement the Java application programming interface (API), and other elements that form a Java Runtime Environment (JRE).

Agent 316 is configured to schedule and coordinate a set of integration tasks associated with one or more integration processes stored in repositories 302. For example, at runtime, an agent coordinates the execution of integration processes. The agent may retrieve code stored in master repository 304, connect to various source and target systems, and orchestrate an overall data integration process or scenario.

Referring again to FIG. 3, ODI Studio 312 includes hardware and/or software elements configured to design data integration projects. In this example, ODI Studio 312 includes four graphical modules or navigators that are used to create and manage data integration projects, namely, designer module 318, operator module 320, topology module 322, and security module 324. Designer module 318 is a module configured to define data stores (tables, files, Web services, and so on), data mappings, and packages (sets of integration steps, including mappings). In various embodiments, designer module 318 defines declarative rules for data transformation and data integrity. Accordingly, project development takes place in designer module 318. Additionally, in designer module 318, is where database and application metadata are imported and defined. Designer module 318, in one embodiment, uses metadata and rules to generate data integration scenarios or load plans for production. In general, designer module 318 is used to design data integrity checks and to build transformations such as for example: automatic reverse-engineering of existing applications or databases, graphical development and maintenance of transformation and integration mappings, visualization of data flows in the mappings, automatic documentation generation, and customization of generated code.

Operator module 320 is a module configured to view and manage production integration jobs. Operator module 320, thus, manages and monitors data integration processes in production and may show execution logs with error counts, the number of rows processed, execution statistics, the actual code that is executed, and so on. At design time, developers can also use operator module 320 for debugging purposes in connection with designer module 318.

Topology module 322 is a module configured to create and manage connections to datasources and agents. Topology module 322 defines the physical and logical architecture of the infrastructure. Infrastructure or projects administrators may register servers, database schemas and catalogs, and agents in a master repository through topology module 322. Security module 324 is a module configured to manage users and their repository privileges.

In general, a user or process interacts with designer module 318 to create a data integration project having one or more data integration processes for sources and targets 326. Each data integration process includes at least one data integration task. In some embodiments, a data integration tasks is defined by a set of business rules indicative of what bit of data is to be transformed and combined with other bits as well as technical specifics of how the data is actually extracted, loaded, and so on. In preferred embodiments, a data integration tasks is specified using a declarative approach to build data mappings. A mapping is an object that populates one datastore, called the target, which data coming from one or more other datastores, known as sources. In general, columns in the source datastore are linked to the columns in the target datastore through mapping. A mapping can be added into a package as a package step. As discussed above, a package defines a data integration job. A package is created under a project and is made up of an organized sequence of steps, each of which can be a mapping or a procedure. A package can have one entry point and multiple exit points.

In some embodiments, when creating a new mapping, a developer or technical business user interacts with designer 318 to first define which data is integrated and which business rules should be used. For example, the developer may specify what tables are to be joined, filters to be applied, and SQL expressions to be used to transform data. The particular dialect of SQL that is used is determined by the database platform on which the code is to be executed. Then, in a separate step, technical staff can interact with designer 318 to choose the most efficient way to extract, combine, and then integrate this data. For example, the technical staff may use database-specific tools and design techniques such as incremental loads, bulk-loading utilities, slowly changing dimensions, and changed-data capture.

In this embodiment, mappings can be created for sources and targets 326. Sources and targets 326 may include one or more legacy applications 328, one or more files/XML documents 330, one or more applications 332, one or more data warehouses (DW), business intelligence (BI) tools and applications, and enterprise process management (EPM) tools and applications 334, and one or more JVMs 336 (including runtime web service 340 and agent 342).

Figure 4:
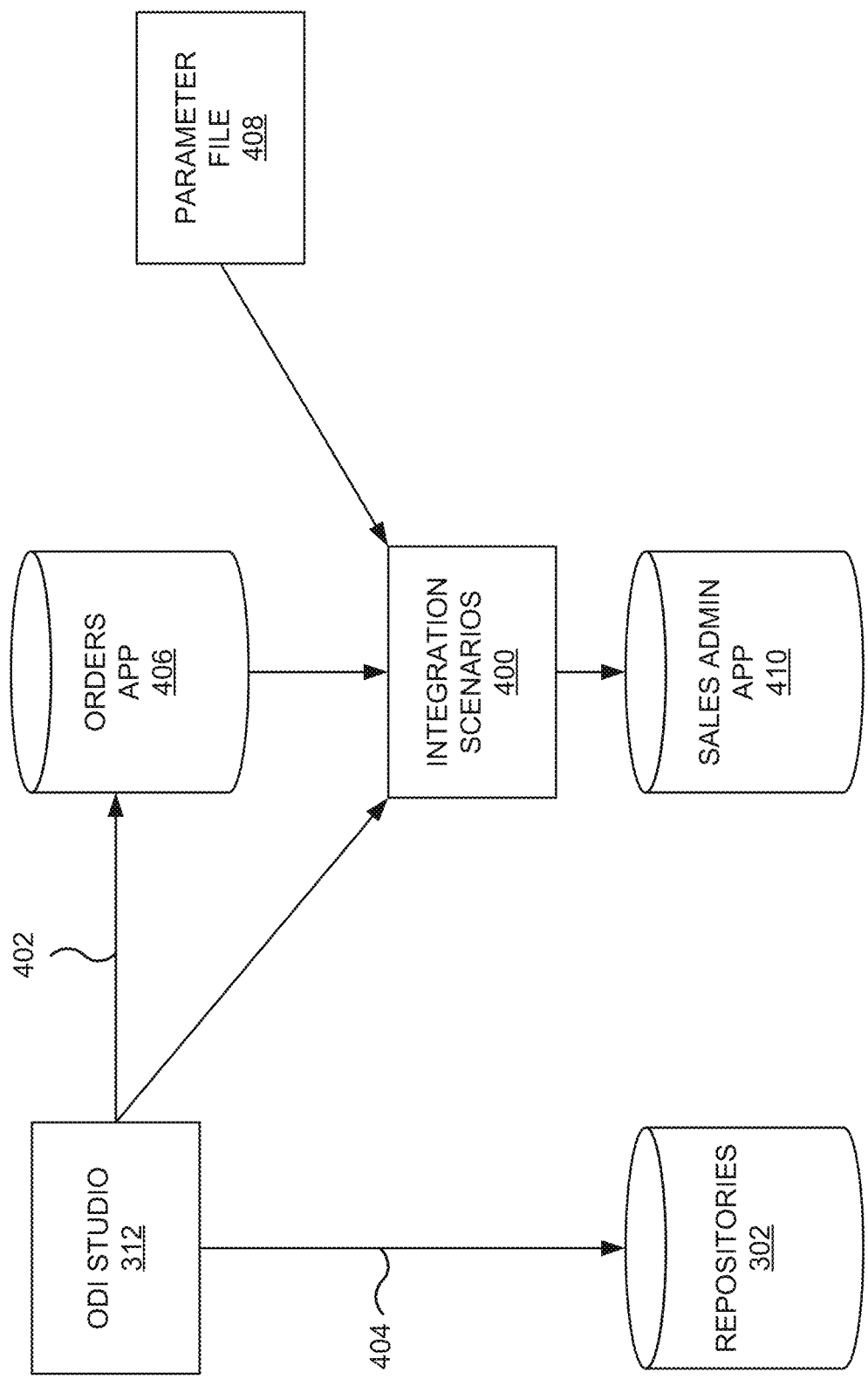
FIG. 4 is a block diagram of an environment having various heterogeneous data sources for which data integration scenarios may be created in various embodiments of the present invention.

FIG. 4 is a block diagram of environment 400 having various heterogeneous data sources for which data integration scenarios may be created in various embodiments of the present invention. In this example, environment 400 includes ODI Studio 312 and repositories 302. Repositories 302 contain all of the metadata required to generate integration scenarios 400. A user or process interacts with ODI Studio 312 to create integration scenarios 400 using data integrity controls 402 and declarative rules 404.

Orders application 406 is representative of an application for tracking customer orders. An "Orders Application" data model is created to represent data stored in Orders application 406 as well as any data integrity controls or conditions. For example, the "Orders Application" data model may be based on a Hyper Structured Query Language Database (HSQLDB) mapping and include five datastores, SRC_CITY, SRC_CUSTOMER, SRC_ORDERS, SRC_ORDER_LINES, SRC_PRODUCT, and SRC_REGION.

Parameter file 408 is representative of a flat file (e.g., ASCII) issued from a production system containing a list of sales representatives and the segmentation of ages into age ranges. In this example, a "Parameter" data model is created to represent the data in the flat file. For example, the "Parameter" data model may be based on a file interface and include two datastores, SRC_SALES_PERSON and SRC_AGE_GROUP.

Sales administration application 410 is representative of an application for tracking sales. The sales administration application 410 may be a data warehouse populated with transformations of data from orders application 406 and parameter file 408. A "Sales Administration" data model is created to represent data stored in sales administration application 410 as well as any data integrity controls or conditions or transformations. For example, the "Sales Administration" data model may be based on a Hyper Structured Query Language Database (HSQLDB) mapping and include six datastores, TRG_CITY, TRG_COUNTRY, TRG_CUSTOMER, TRG_PRODUCT, TRG_PROD_FAMILY, TRG_REGION, and TRG_SALE.

Figure 5A:
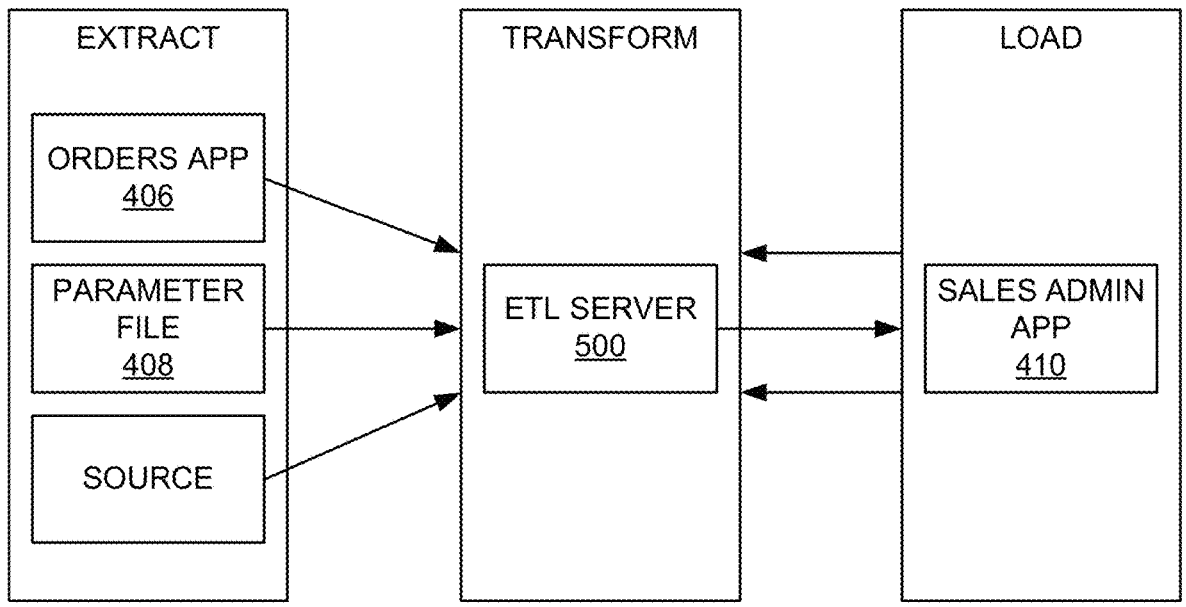
FIGS. 5A and 5B depict simplified data flows in conventional data integration processing that may be performed by the data integration system.
Figure 5B:
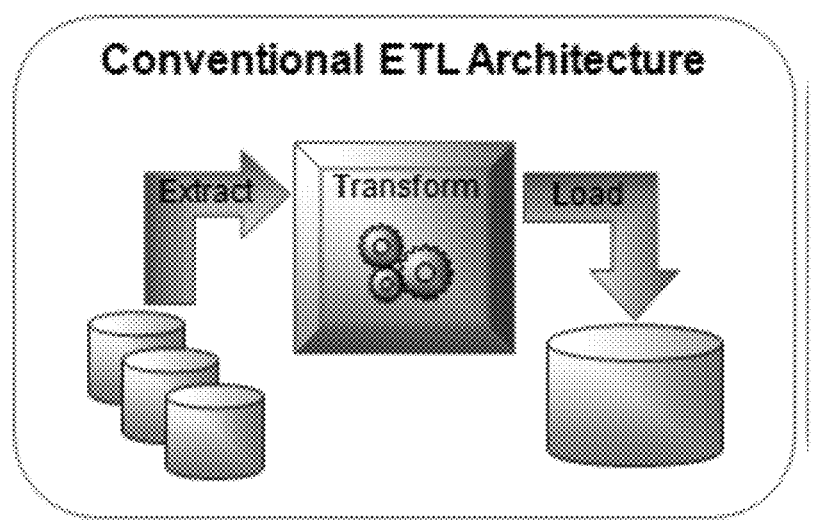

FIGS. 5A and 5B depict simplified data flows in conventional data integration processing that may be performed by data integration system 200. In this example, data from orders application 406, parameter file 408, and one or more other optional or additional sources flow through a traditional ETL process targeted to sales administration application 410. Data transforms occur in a separate ETL server 500. The scenario requires dedicated or proprietary resources, results in poorer performance, and incurs high costs.

Figure 6A:
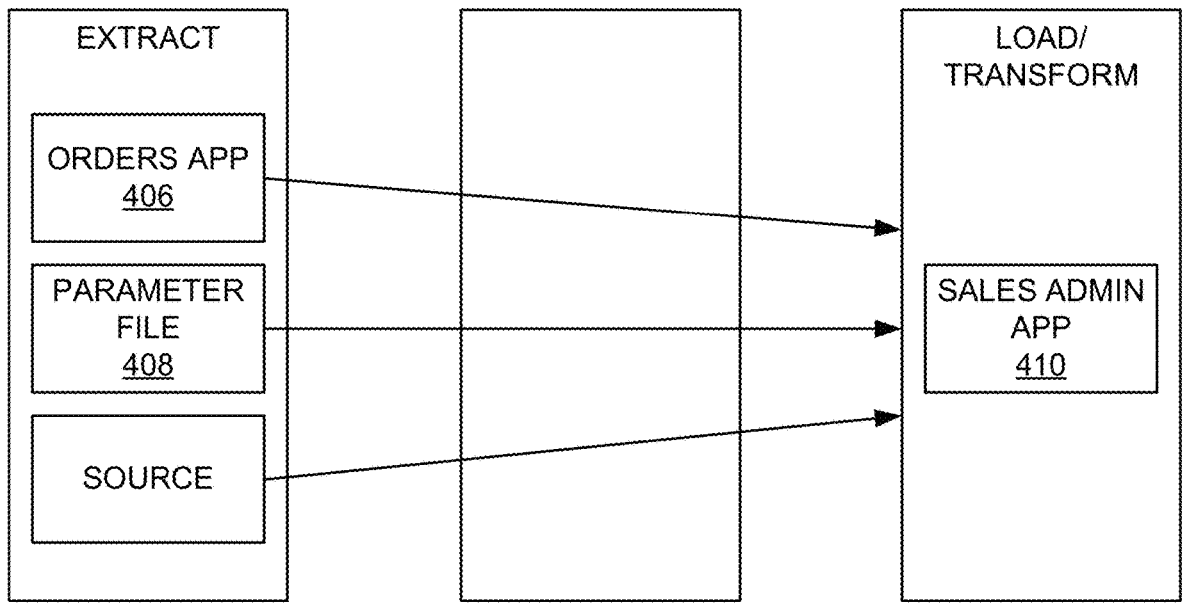
FIGS. 6A and 6B depict simplified data flows in next generation data integration processing that may be performed by the data integration system, in accordance with an embodiment of the present invention.
Figure 6B:
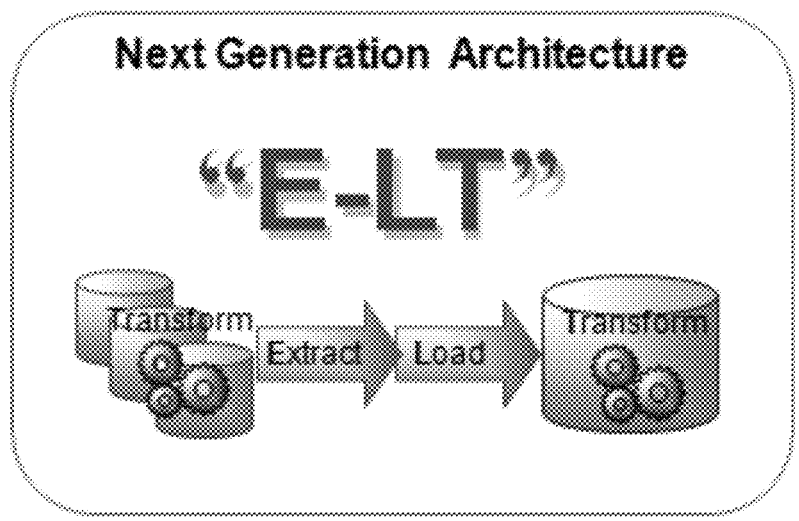

FIGS. 6A and 6B depict simplified data flows in next generation data integration processing that may be performed by data integration system 200, in accordance with an embodiment of the present invention. In this example, data from orders application 406, parameter file 408, and one or more other optional or additional sources flow through E-LT process targeted to sales administration application 410. Data transforms leverage existing resources resulting in higher performance and efficiency. As described above, prior ETL systems required dedicated and/or proprietary infrastructure to perform data transforms. This was done, in part, to accommodate unknown user infrastructures. For example, without knowing what types of databases are being used, prior ETL systems were unable to anticipate what transform operations would be available in a given system. However, this results in under-utilized resources, such as the user's existing databases and servers which are capable of executing the appropriate data transforms without any dedicated and/or proprietary infrastructure.

In accordance with an embodiment, the present invention leverages the user's existing infrastructure by enabling the user to customize a data integration process according to the user's particular needs. For example, when a data integration plan is designed, it can be divided into discrete portions which are executable by a single system, referred to as execution units. Once a data integration plan has been divided into a plurality of execution units, the user can be presented with a physical plan based on the user's infrastructure and system resources. This plan can be further customized by the user to change which user systems execute which execution units. For example, a user may be presented with a plan in which a join operation is executed on a first database, and the user may customize the plan by moving the join operation to a second database.

As shown in FIG. 6B, this results in an extract-load-transform (E-LT) architecture that does not rely on a stand-alone transform server which characterized prior ETL systems. Instead, as described above, data transforms can be performed on the user's existing infrastructure. The E-LT architecture provides users with greater flexibility while reducing costs associated with acquiring and maintaining proprietary transform servers.

Referring again to FIG. 3, agents can be used to schedule and coordinate a set of integration tasks associated with an integration process. For example, at runtime, an agent coordinates the execution of integration processes. The agent may retrieve code stored in master repository 304, connect to the various source and target systems and orchestrates an overall data integration process or scenario. In various embodiments, there are two types of agents. In one example, a standalone agent is installed on desktop 308, such as agent 316. In another example, an application server agent can be deployed on application server 326 (such as a Java EE Agent deployed on an Oracle WebLogic Server) and can benefit from the application server layer features such as clustering for High Availability requirements. In yet another example, an agent can be deployed on sources and targets 326, such as agent 342.

In this embodiment, data integration system 200 includes application server 344 that may include one or more of the above discussed agents. Application server 344 is representative of one or more application servers, web-servers, or hosted applications. In this example, application server 344 includes FMW console 346, servlet container 348, web services container 350, and data sources connection pool 352.

FMW console 346 is representative of one or more hardware and/or software elements configured to manage aspects of application server 344, such as information related to servlet container 348, web services container 350, and data sources connection pool 334. For example, FMW console 346 may be a browser-based, graphical user interface used to manage an Oracle WebLogic Server domain. FMW console 346 may include functionality to configure, start, and stop WebLogic Server instances, configure WebLogic Server clusters, configure WebLogic Server services, such as database connectivity (JDBC) and messaging (JMS), configure security parameters, including creating and managing users, groups, and roles, configure and deploy Java EE applications, monitor server and application performance, view server and domain log files, view application deployment descriptors, and edit selected run-time application deployment descriptor elements. In some embodiments, FMW console 346 includes ODI plug-in 354 providing FMW console 346 with access to data integration processes in production and may show execution logs with error counts, the number of rows processed, execution statistics, the actual code that is executed, and so forth.

Servlet container 348 is representative of one or more hardware and/or software elements configured to extend the capabilities of application server 344. Servlets are most often used to process or store data that was submitted from an HTML form, provide dynamic content such as the results of a database query, and manage state information that does not exist in the stateless HTTP protocol, such as filling the articles into the shopping cart of the appropriate customer. A servlet is typically a Java class in Java EE that conforms to the Java Servlet API, a protocol by which a Java class may respond to requests. To deploy and run a servlet, servlet container 348 is used as a component of a web server that interacts with servlets. Accordingly, servlet container 348 may extend functionality provided by public web service 356 and data services 358 of web services container 350 as well as access to data pools provided by data sources connection pool 352. Servlet container 348 is also responsible for managing the lifecycle of servlets, mapping a URL to a particular servlet and ensuring that the URL requester has the correct access rights.

In this example, servlet container 348 includes Java EE application 360 associated with ODI SDK 362, ODI console 364, and runtime web service 366 associated with Java EE agent 368. ODI SDK 362 provides a software development kit (SDK) for data integration and ETL design. ODI SDK 362 enables automation of work that is common and very repetitive allowing a user to script repetitive tasks.

ODI console 364 is a Java Enterprise Edition (Java EE) application that provides Web access to repositories 302. ODI console 364 is configured to allow users to browse Design-Time objects, including projects, models, and execution logs. ODI console 364 may allow users to view flow maps, trace the source of all data, and even drill down to the field level to understand the transformations used to build the data. In addition, end users can launch and monitor scenario s execution through ODI console 364. In one aspect, ODI console 364 provides administrators with the ability to view and edit Topology objects such as Data Servers, Physical and Logical Schemas as well as to manage repositories 302.

Data Scenario Design and Development

As discussed above, a scenario is designed to put a source component (mapping, package, procedure, variable) into production. A scenario results from the generation of code (SQL, shell, and so forth) for this component. A scenario can be exported and then imported into different production environments.

Figure 7:
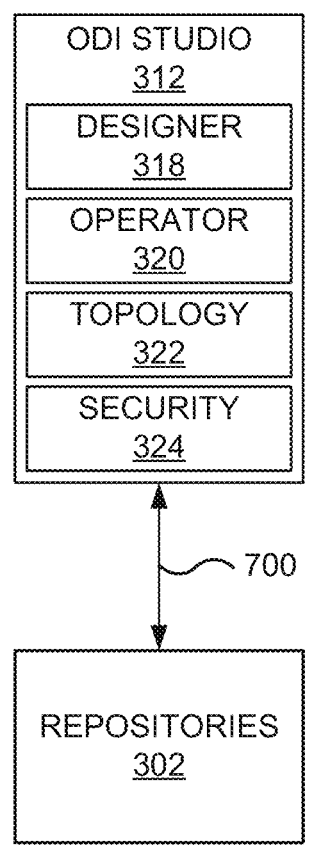
FIG. 7 is a simplified block diagram of interactions between an ODI Studio and a repository of the data integration system in one embodiment according to the present invention.

FIG. 7 is a simplified block diagram of interactions between an ODI Studio and a repository of the data integration system in one embodiment according to the present invention. In the embodiment shown in FIG. 7, ODI Studio 312 of FIG. 3 uses metadata and rules to generate data integration scenarios 700 for production. In general, designer module 318 is used to design data integrity checks and to build transformations such as for example: automatic reverse-engineering of existing applications or databases, graphical development and maintenance of transformation and integration mappings, visualization of data flows in the mappings, automatic documentation generation, and customization of generated code.

Figure 8:
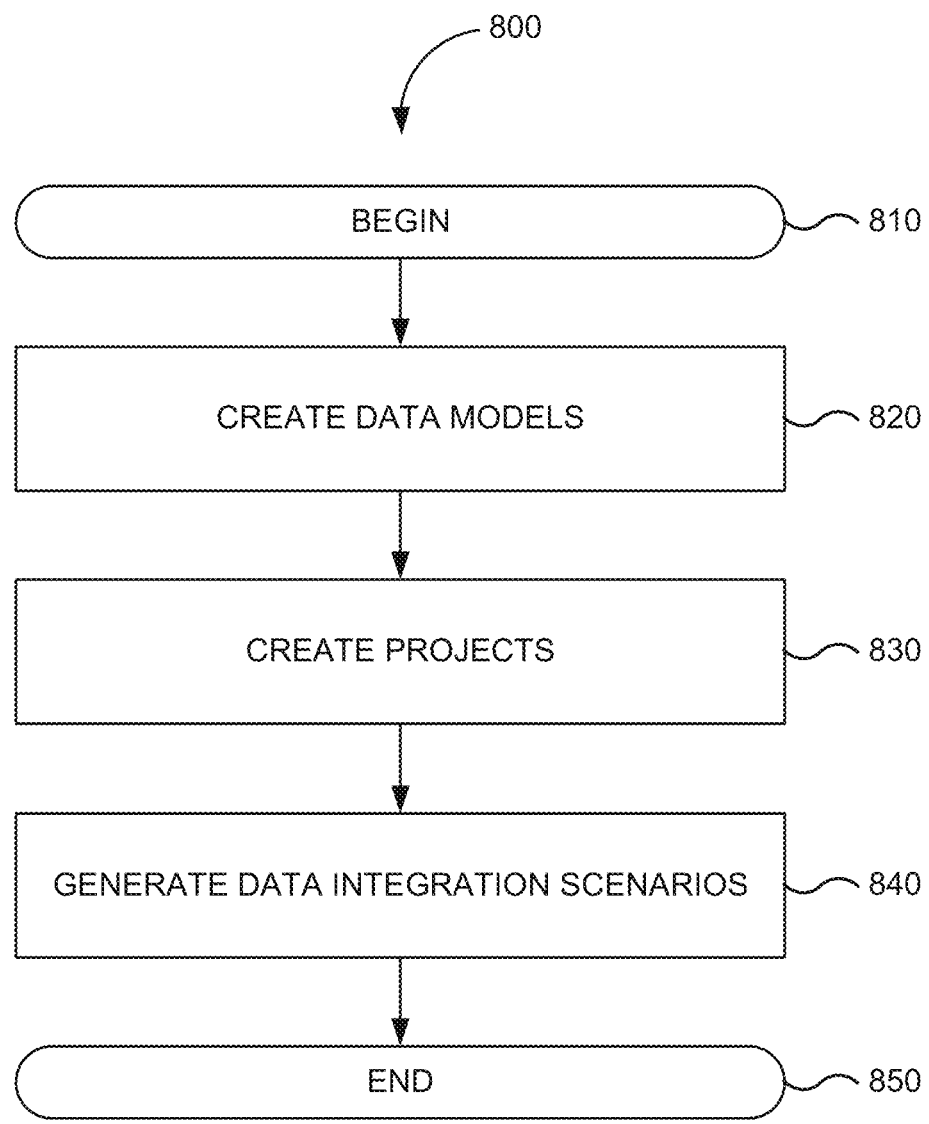
FIG. 8 depicts a flowchart of a method for creating a data integration scenario in accordance with an embodiment of the present invention.

FIG. 8 depicts a flowchart of method 800 for creating a data integration scenario in accordance with an embodiment of the present invention. Implementations of or processing in method 800 depicted in FIG. 8 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 800 depicted in FIG. 8 begins in step 810.

In various embodiments, a user may initiate a session with designer module 318 of ODI Studio 312 and connect to repositories 302. The user may interact with one or more user interface features to create a new data integration project or select from existing data integration projects stored in, for example, master repository 304. In general, designer module 318 is used to manage metadata, to design data integrity checks, and to build transformations. In various embodiments, the main objects handled through designer module 318 are models and projects. Data models contain all of the metadata in a data source or target (e.g., tables, columns, constraints, descriptions, cross-references, etc.). Projects contain all of the loading and transformation rules for a source or target (e.g., mappings, procedures, variables, etc.)

Figure 9:
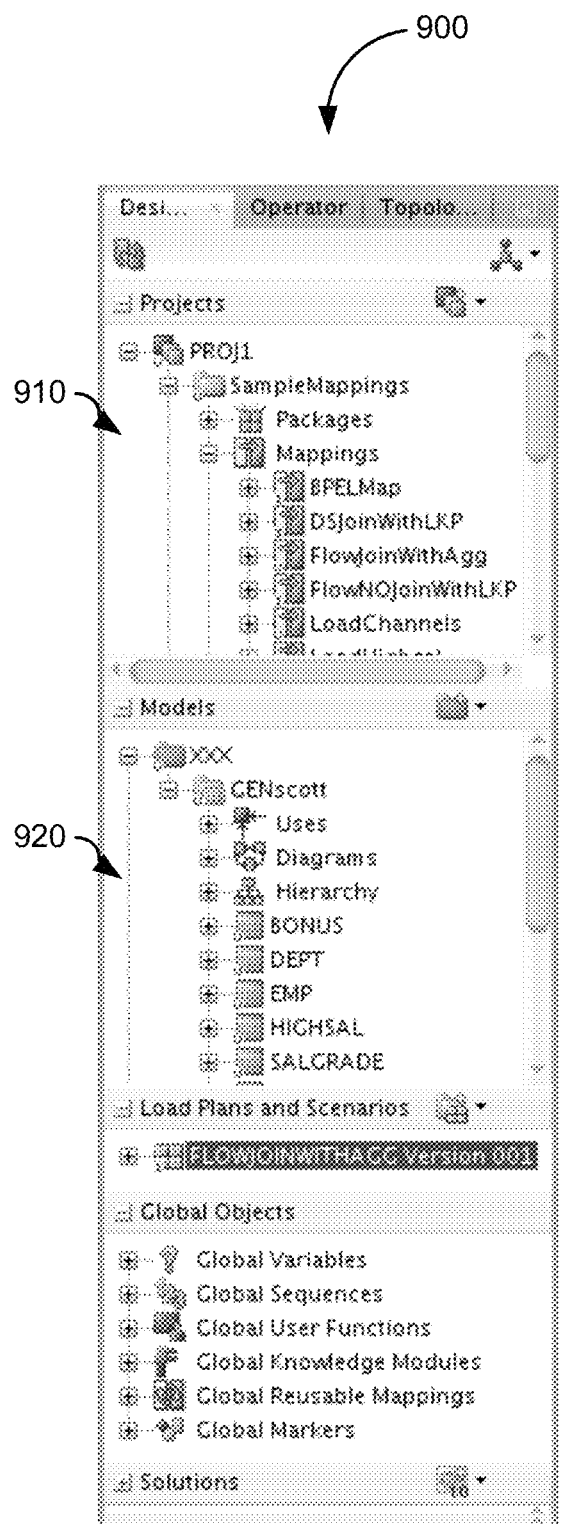
FIG. 9 is a screenshot of a user interface for creating data integration scenarios in accordance with an embodiment of the present invention.

In step 820, one or more data models are created. In step 830, one or more projects are created. FIG. 9 is a screenshot of user interface 900 for creating a data integration scenario in accordance with an embodiment of the present invention. In this example, navigation panel 910 displays information and includes functionality for interacting with projects. Navigation panel 920 displays information and includes functionality for interacting with data models. As discussed above, the user may not only create the data model, but also develop any data integrity checks for the data in the data models. Additionally, the user may specify mappings, procedures, variables for projects that provide data integrity and transforms for the data in a flow that loads data from a source into a target. In step 840, one or more data integration scenarios are generated. FIG. 8 ends in step 850.

Figure 10:
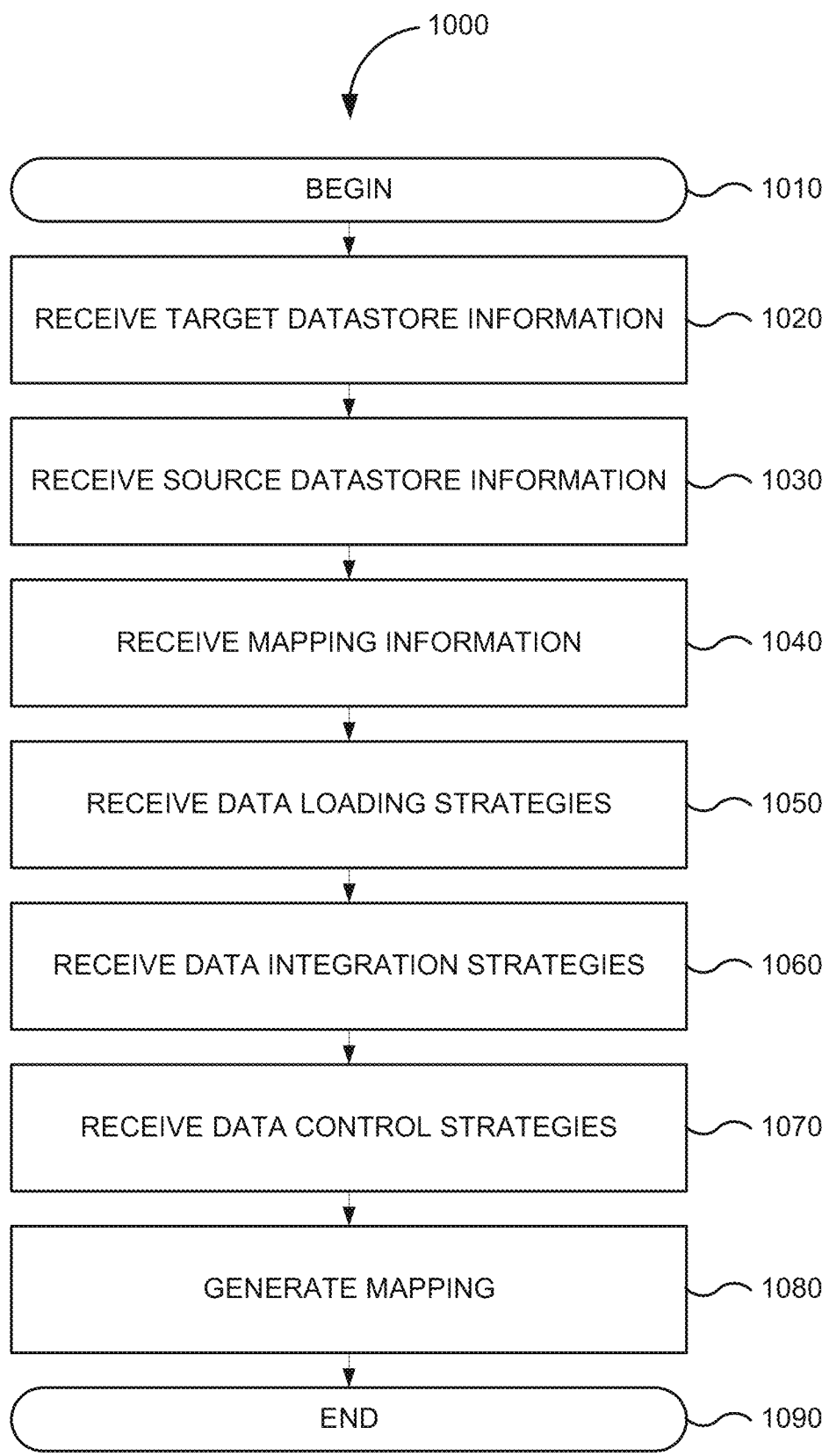
FIG. 10 depicts a flowchart of a method for creating a mapping in accordance with an embodiment of the present invention.

FIG. 10 depicts a flowchart of method 1000 for creating a mapping in accordance with an embodiment of the present invention. Implementations of or processing in method 1000 depicted in FIG. 10 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 1000 depicted in FIG. 10 begins in step 1010.

In step 1020, target datastore information is received. For example, a user may interact with one or more user interface features of designer module 318 to provide target datastore information. In one embodiment, the user may drag and drop target datastore information comprising one or more data models from navigation panel 910 onto a mapping or flow panel that visually represents aspects of a selected data model and any associated transforms or data integrity checks.

In step 1030, source datastore information is received. For example, a user may interact with one or more user interface features of designer module 318 to provide source datastore information. In one embodiment, the user may drag and drop source datastore information comprising one or more data models from navigation panel 910 onto the same mapping or flow panel of the target datastore information that visually represents aspects of a selected data model and any associated transforms or data integrity checks.

In various embodiments, the source datastore information and the target data store information may be composed of one or more data models and optionally operations. Some examples of operations can include one or more data set operations (e.g., unions, joins, intersections, etc.), data transformations, data filter operations, constraints, descriptions, cross-references, integrity checks, or the like. In further embodiments, some of these operations may be preconfigured and visually represented in designer module 318. In other embodiments, custom operations may be provided allowing the user to specify logic, mappings, and the like that implement an operation.

In step 1040, mapping information is received. For example, a user may interact with one or more user interface features of designer module 318 to map the source datastore information to the target datastore information. In one embodiment, the user may visually connect attributes of data elements in the source datastore information with attributes of data elements in the target datastore information. This may be done by matching column names of tables in the source datastore information and the target datastore information. In further embodiments, one or more automatic mapping techniques may be used to provide mapping information.

Figure 11:
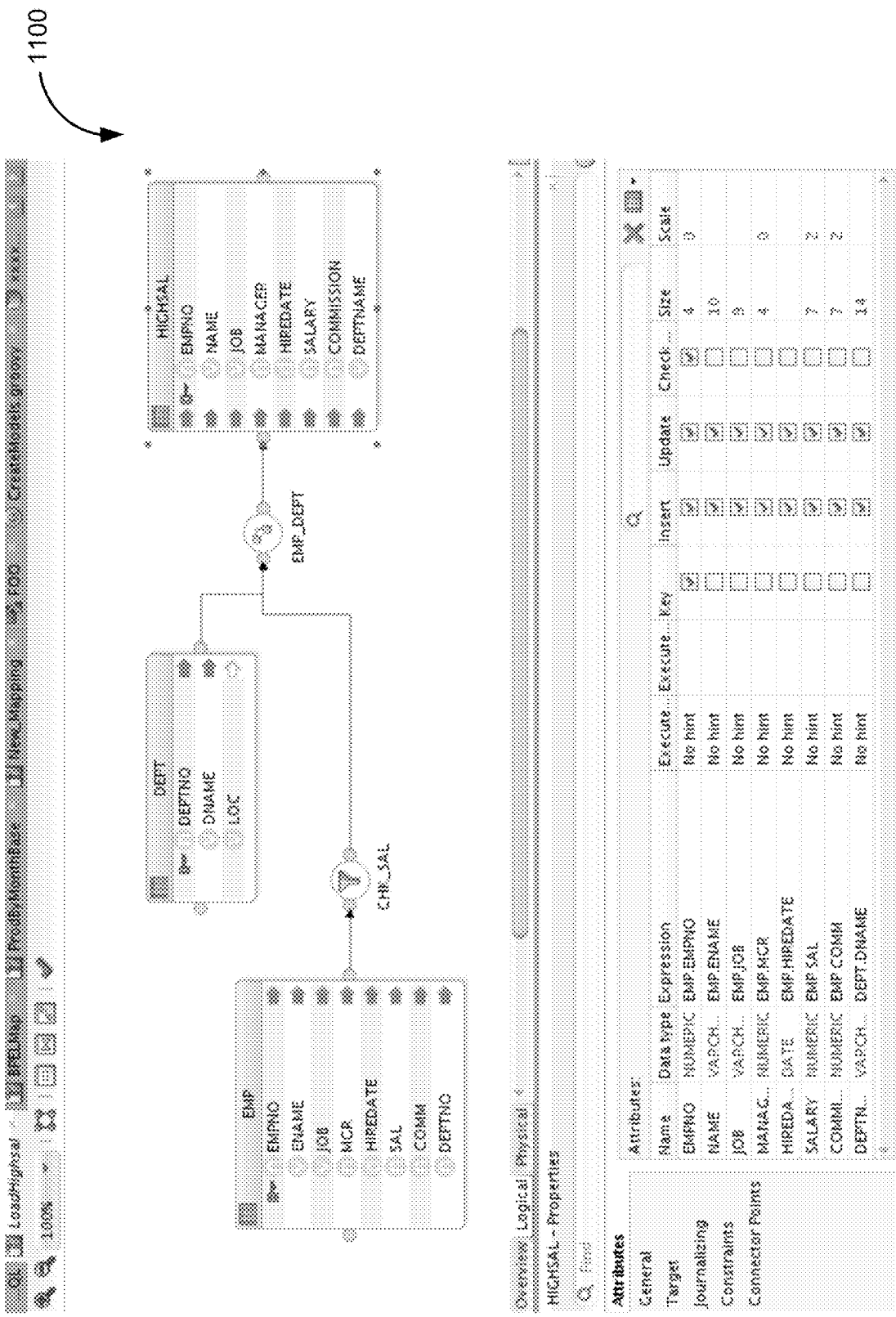
FIG. 11 is a screenshot of a user interface for providing mapping information in data integration scenarios in accordance with an embodiment of the present invention.

FIG. 11 is a screenshot of user interface 1100 for providing mapping information in a data integration scenario in accordance with an embodiment of the present invention. In this example, attributes of source components are mapped to attributes of target components.

Referring again to FIG. 10, in step 1050, data loading strategies are received. A data loading strategy includes information on how the actual data from the source datastore information is to be loaded during an extract phase. Data loading strategies can be defined in a flow tab of designer 318. In some embodiments, a data loading strategy can be automatically computed for a flow depending on a configuration of the mapping.

For example, one or more knowledge modules may be proposed for the flow. A knowledge module (KM) is a component that implements reusable transformation and ELT (extract, load, and transform) strategies across different technologies. In one aspect, knowledge modules (KMs) are code templates. Each KM can be dedicated to an individual task in an overall data integration process. The code in KMs appears in nearly the form that it will be executed with substitution methods enabling it to be used generically by many different integration jobs. The code that is generated and executed is derived from the declarative rules and metadata defined in the designer module 318. One example of this is extracting data through change data capture from Oracle Database 10g and loading the transformed data into a partitioned fact table in Oracle Database 11g, or creating timestamp-based extracts from a Microsoft SQL Server database and loading this data into a Teradata enterprise data warehouse.

The power of KMs lies in their reusability and flexibility—for example, a loading strategy can be developed for one fact table and then the loading strategy can be applied to all other fact tables. In one aspect, all mappings that use a given KM inherit any changes made to the KM. In some embodiments, five different types of KMs are provided, each of them covering one phase in a transformation process from source to target, such as an integration knowledge module (IKM), a loading knowledge module (LKM), and a check knowledge module CKM.

Referring to FIG. 4, a user may define a way to retrieve the data from SRC_AGE_GROUP, SRC_SALES_PERSON files and from the SRC_CUSTOMER table in environment 400. To define a loading strategies, a user may select a source set that corresponds to the loading of the SRC_AGE_GROUP file and select a LKM File to SQL to implement the flow from a file to SQL. In one aspect, a LKM is in charge of loading source data from a remote server to a staging area.

In step 1060, data integration strategies are received. After defining the loading phase, the user defines a strategy to adopt for the integration of the loaded data into a target. To define the integration strategies, the user may select a target object and select a IKM SQL Incremental Update. An IKM is in charge of writing the final, transformed data to a target. When an IKM is started, it assumes that all loading phases for remote servers have already carried out their tasks, such as having all remote source data sets loaded by LKMs into a staging area, or the source datastores are on the same data server as the staging area.

In step 1070, data control strategies are received. In general, an CKM is in charge of checking that records of a data set are consistent with defined constraints. An CKM may be used to maintain data integrity and participates in overall data quality initiative. A CKM can be used in 2 ways. First, to check the consistency of existing data. This can be done on any datastore or within mappings. In this case, the data checked is the data currently in the datastore. In a second case, data in the target datastore is checked after it is loaded. In this case, the CKM simulates the constraints of the target datastore on the resulting flow prior to writing to the target.

Figure 12:
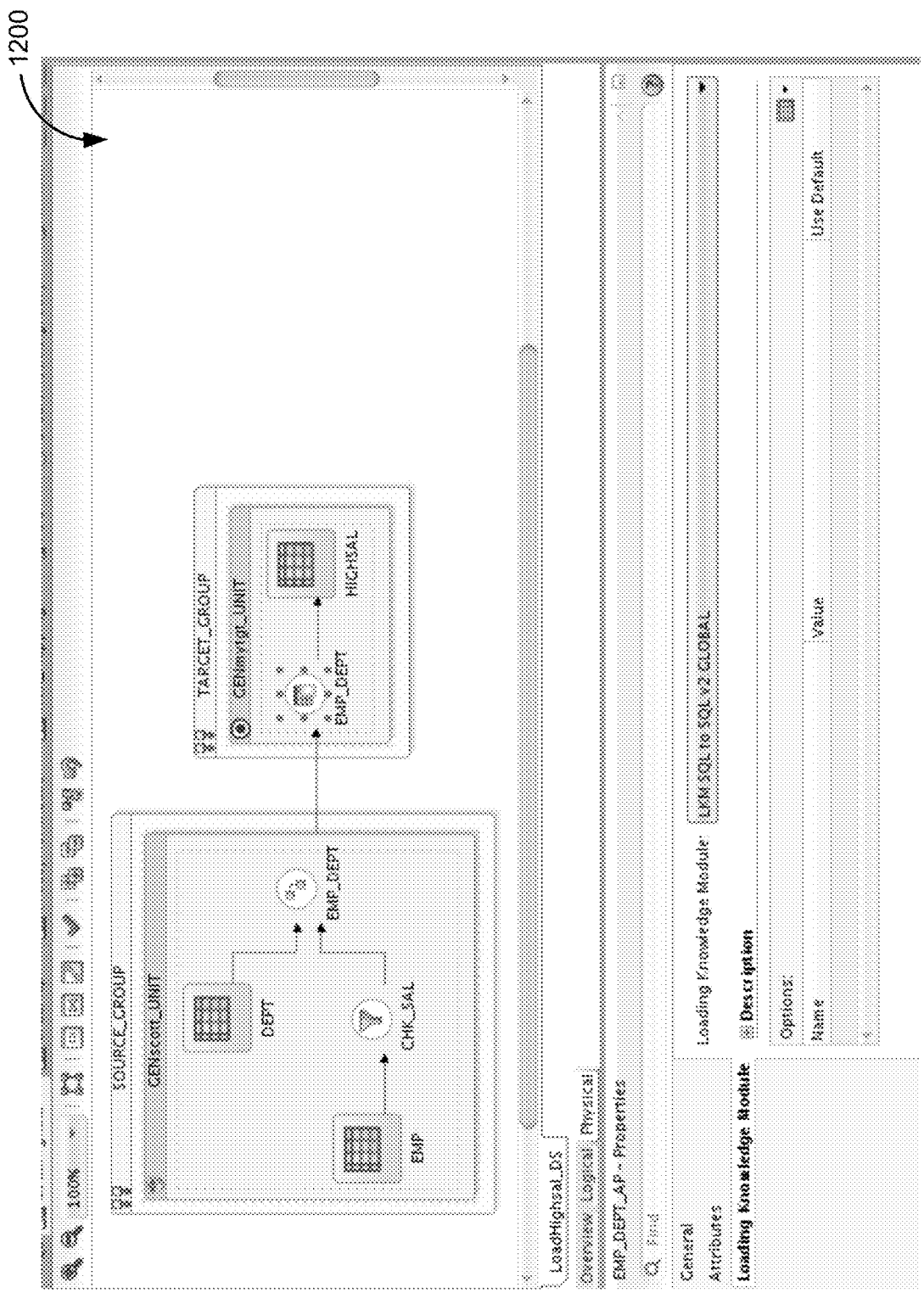
FIG. 12 is a screenshot of a user interface for providing flow information in data integration scenarios in accordance with an embodiment of the present invention.

FIG. 12 is a screenshot of user interface 1200 for providing flow information in a data integration scenario in accordance with an embodiment of the present invention.

In step 1080, a mapping is generated. FIG. 10 ends in step 1090.

Data Integration Scenario Packages and Deployment

As discussed above, automation of data integration flows can be achieved in data integration system 200 by sequencing the execution of the different steps (mappings, procedures, and so forth) in a package and by producing a production scenario containing the ready-to-use code for each of these steps. A package is made up of a sequence of steps organized into an execution diagram. Packages are the main objects used to generate scenarios for production. A scenario is designed to put a source component (mapping, package, procedure, variable) into production. A scenario results from the generation of code (SQL, shell, and so forth) for this component. A scenario can be exported and then imported into different production environments.

Figure 13:
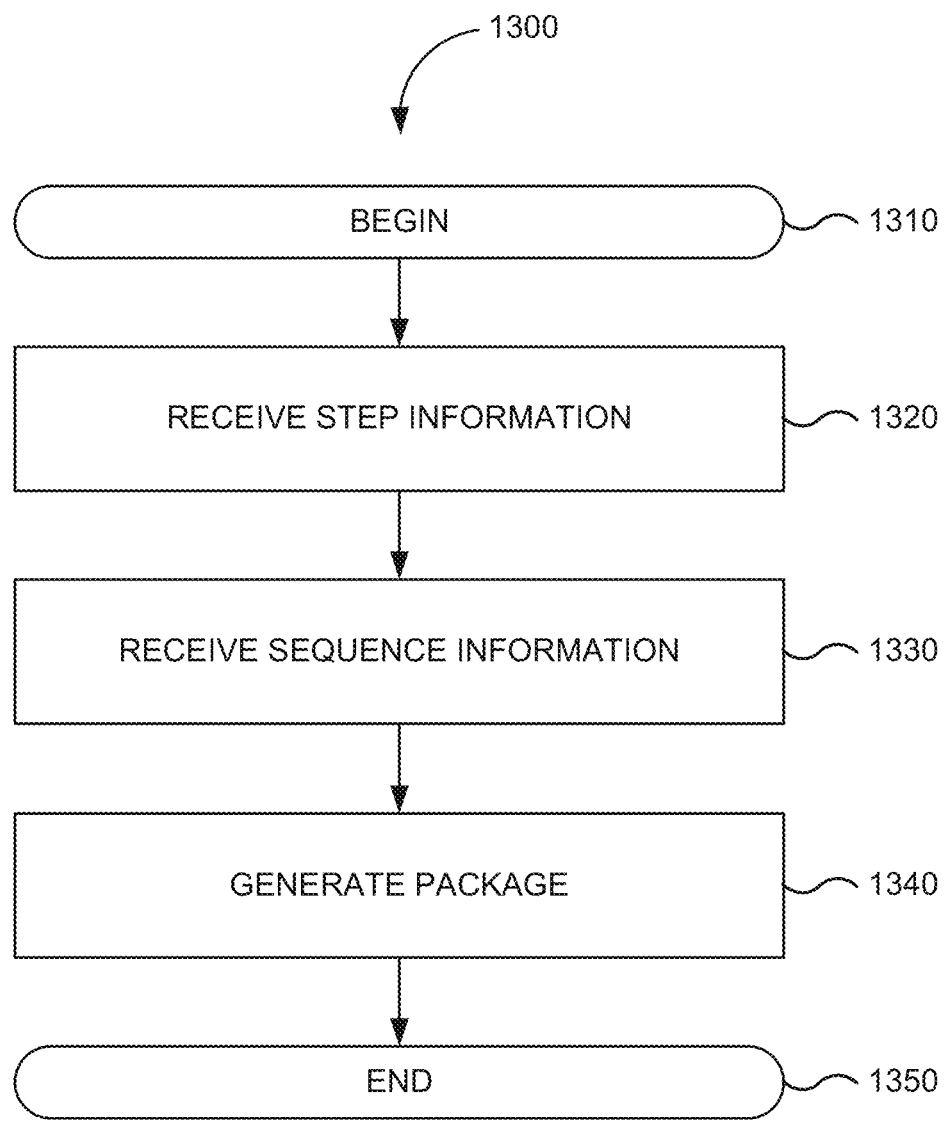
FIG. 13 depicts a flowchart of a method for creating a package in accordance with an embodiment of the present invention.

FIG. 13 depicts a flowchart of a method for creating a package in accordance with an embodiment of the present invention. Implementations of or processing in method 1300 depicted in FIG. 13 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 1300 depicted in FIG. 13 begins in step 1310.

In step 1320, step information is received. Package step information includes information identifying a step, elements, properties, components, and the like. In one example, a user may interact with one or more user interface features of designer module 318 to create, identify, or otherwise specify one or more steps for a package. In one embodiment, one or more components are selected and placed on a diagram. These components appear as steps in the package.

In step 1330, step sequence information is received. Package step sequence information includes information identifying an ordering for a step, dependencies, and the like. Once steps are created, the steps are ordered or reorder into a data processing chain. In one example, a user may interact with one or more user interface features of designer module 318 to provide sequencing or ordering for one or more steps of a package. A data processing chain may include a unique step defined as a first step. Generally, each step has one or more termination states, such as success or failure. A step in some states, such as failure or success, can be followed by another step or by the end of the package. In one aspect, in case of some states, such as failure, sequence information may define a number of retries. In another aspect, a package may have but several possible termination steps.

Figure 14:
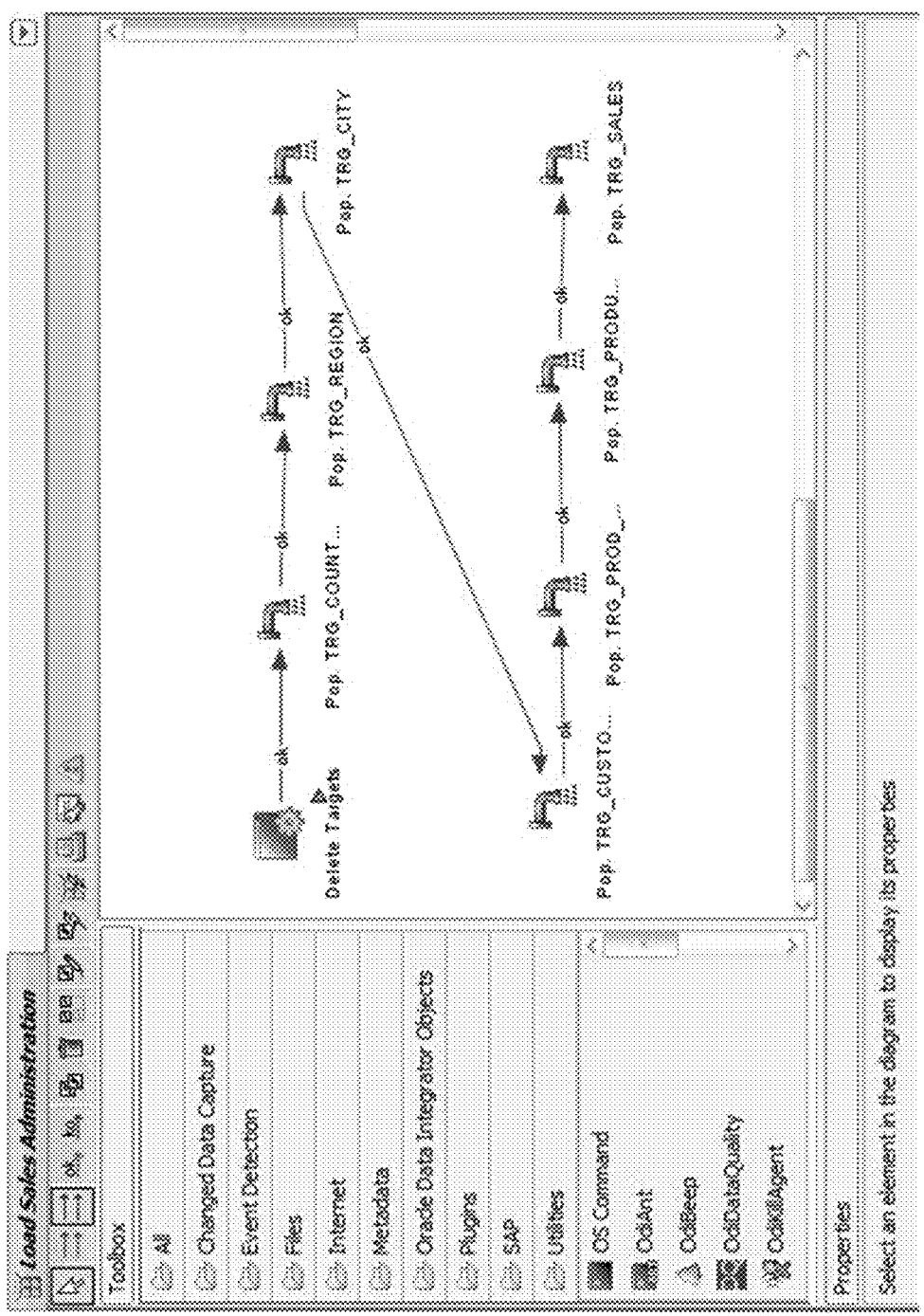
FIG. 14 is a screenshot of a user interface for providing package sequence information in a data integration scenario in accordance with an embodiment of the present invention.

FIG. 14 is a screenshot of a user interface for providing package sequence information in a data integration scenario in accordance with an embodiment of the present invention.

In step 1340, a package is generated. FIG. 13 ends in step 1350.

As discussed above, the automation of data integration flows can be achieved by sequencing the execution of different steps (mappings, procedures, and so forth) in a package. The package can then be produced for a production scenario containing the ready-to-use code for each of the package's steps. In various embodiments, the package is deployed to run automatically in a production environment.

Figure 15:
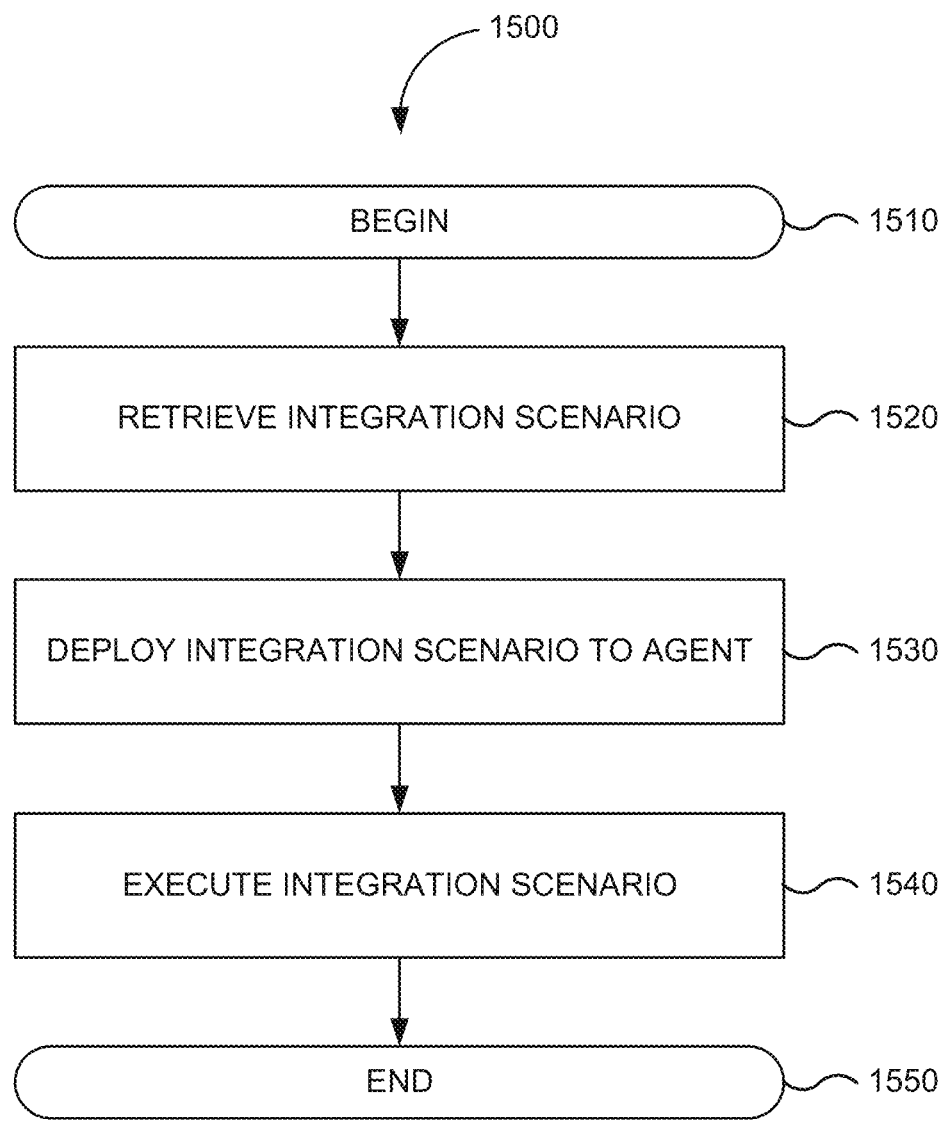
FIG. 15 depicts a flowchart of a method for deploying a data integration scenario in accordance with an embodiment of the present invention.

FIG. 15 depicts a flowchart of method 1500 for deploying a data integration scenario in accordance with an embodiment of the present invention. Implementations of or processing in method 1500 depicted in FIG. 15 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 1500 depicted in FIG. 15 begins in step 1510.

In step 1520, an integration scenario is retrieved. In one embodiment, a package is retrieved from repositories 302. In step 1530, the integration scenario is deployed to one or more agents. In step 1540, the integration scenario is executed by the one or more agents. In one aspect, the integration scenario can be executed in several ways, such as from ODI Studio 312, from a command line, or from a web service. Scenario execution can be viewed and monitored, for example, via operator module 320 and the like as discussed above. FIG. 15 ends in step 1550.

Load Plan Generation

In various embodiments, data integration projects are designed to define data stores (tables, files, Web services, and so on), data mappings, and packages (sets of integration steps, including mappings). Metadata and rules can be used to generate data integration scenarios or load plans for production. As discussed above, designer module 318 can be used to design data integrity checks and to build transformations such as for example: automatic reverse-engineering of existing applications or databases, graphical development and maintenance of transformation and integration mappings, visualization of data flows in the mappings, automatic documentation generation, and customization of generated code.

With the introduction of ODI, new methods of orchestrating the tasks of loading data warehouses can be provided. Load plan generator (LPG) is a utility for generating ODI load plans for a desired subset of fact tables to be populated into BIAPPS Data Warehouse against one or more source systems. An ODI load plan is an executable object in ODI that organizes tasks based on pre-defined order on the basis of the fact tables being loaded. LPG is invoked from Configuration Manager (CM) and makes use of metadata stored in CM and ODI repository. There is no separate repository required for LPG. This results in significantly lower metadata development and maintenance costs as LPG uses same metadata as in the ETL tool repository.

At the top of the BIAPPS taxonomy are the different offerings available such as Financial Analytics, HR, CRM, etc. Under the offerings are the functional areas such as accounts payable in finance or payroll in HR. Below the functional areas are the different fact groups like "AP Transactions and Balance" or "Payroll Balance". For each fact group, there are dimension groups associated with it. A dimension group can be specific to a particular fact group or shared across different fact group. The BI apps taxonomy drives both load plan generation as well as the setup flows in Functional Setup manager.

Offering (contains)→
   Functional Areas (contains)→
   Fact Groups (associated to)→
     Dimension Groups As for BIAPPS load phases, there are 3 main phases: Source Data Extract (SDE), Source Independent Load (SIL), and Post Load Process (PLP). The SDE phase consists of tasks extracting data from different source systems. This phase loads all staging tables and requires source system downtime. The SIL phase loads data from staging tables into their respective dimension or fact tables. The PLP phase loads data into aggregate tables or some other facts requiring additional data processing. The SIL and PLP phase requires data warehouse downtime to complete the load process. With a clear separation of SDE and SIL/PLP phases it's possible to control and optimize the source system/warehouse downtime to the corresponding phases.

The LPG deals with the design time dependencies and run time dependencies separately. Any intra-entity specific design time dependencies are seeded in the repository. For example, if a dimension has multiple steps to load the target table in SIL phase, these steps are seeded once in the ODI repository as they are known at design time and never change. The run time dependencies i.e. association of dimension to fact, or association of a dimension or fact to corresponding staging tables on the basis of sources are calculated by the LPG.

This approach reduces the number of iterations and the metadata required to get task ordering correct at the entire graph level as the design time dependencies are always consistently honored.

In various embodiments, load plans can be generated automatically based on definitions obtained from users and load plan components in ODI. A load plan generator (LPG) may be embodied as a BIAPPS utility for generating ODI load plans based on desired subset of fact tables for loading BIAPPS Data Warehouse. This load plan generation application utilizes features in ODI for orchestrating execution of packages. The generated ODI load plan orchestrates execution of tasks in the required order. In one aspect, the LPG is integrated with a configuration manager (CM) which enables users to create load plan definition based on the required subset of fact tables.

LPG then creates one or more ODI load plan objects based on the load plan definitions. Load plan components can be stitched together by LPG to create one or more load plans for loading chosen fact groups in the data warehouse sourcing from different transaction systems. In another aspect, design time and run time dependencies are automatically resolved (e.g., of dimension groups and other auxiliary tables (TMP/PS) based on fact groups) to improve BIAPP deployment and simplify load plan generation. The LPG does not require its own repository and provides a guided list of configurations steps and checklists.

In various embodiments, a setup manager captures user input for fact groups and source system type for a load plan. Load plan generation is then based on load plan components that contain end-to-end load of a data warehouse sourcing from all possible types of transaction systems. These components are not used for the actual loading of the warehouse but configured dynamically based upon load plan rules and the input provided by users during setup. BI developers can create load plan components resolving local dependencies (within a fact group or dimension group). Container load plans can be developed at the grain of phase, source system, dimension group, and fact group. Cross fact group or dimension group dependencies can then be automatically derived.

As discussed above, the load plan components capture the design time dependencies. There is a load plan component per dimension or fact per phase in general. Load plan components are used as building blocks by LPG to generate a complete load plan. Load plan components are further classified into two categories. First, development components are defined at the grain of fact groups or dimension groups as described earlier. Each component contains one or more references to actual ODI scenarios. Each development component requires all steps for loading a particular dimension or fact group. The order of scenarios is pre-defined during development. Most of the development components are for a specific dimension or fact group. However, there are also those defined for supporting tables like persistent staging or general tables. Second, system components are defined to capture the phases and ordering of phases. The system components are mostly static, since BIAPPS load phases rarely change. For special cases, the dependencies across dimension groups and fact groups are defined here. Also, inclusion of support tables such as persistent staging table is controlled here. System components contain references to development components.

In one aspect, a separate load plan is generated for each execution plan defined by users. The generated load plan contains the steps required to load the data warehouse for the selected list of fact groups in the execution plan. The steps can be selected from a variety of preconfigured components and adapted dynamically to a user's scenario. For example, the load plan generator can extract necessary metadata from load plan components to determine which steps are required for an execution plan. The load plan generator application can also utilize ODI SDK's to create a subset load plan at a customer site via S&C manager or ODI plugin.

As mentioned earlier, LPG is invoked from CM and generating a load plan is a two-step process. First, a user creates a load plan definition using CM. A load plan definition is mainly a list of one or more fact groups per source system which the user desires to load. The user then invokes LPG to generate a load plan based on this load plan definition. When complete, the generated load plan is stored back in a load plan folder in ODI repository.

Figure 16:
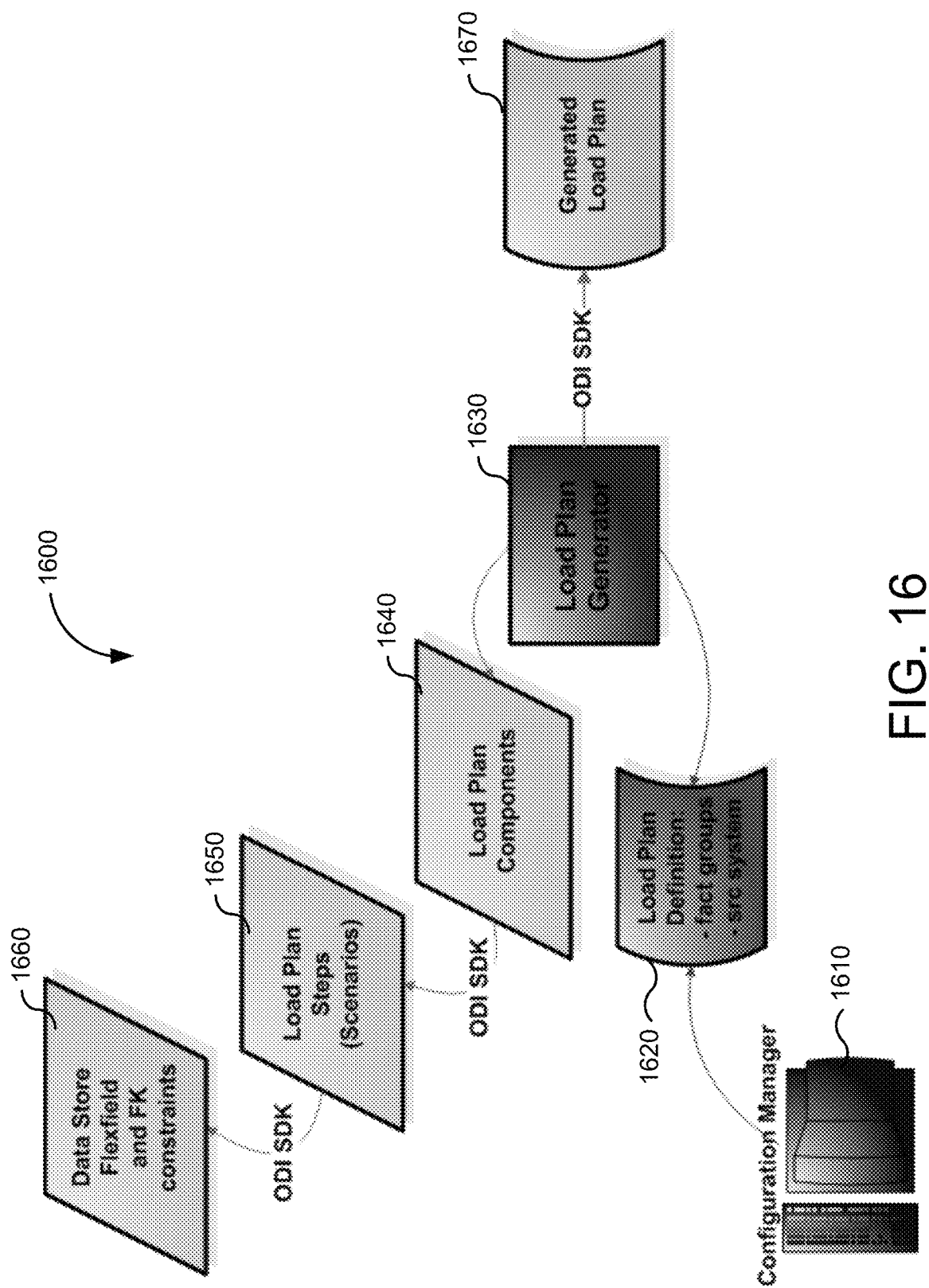
FIG. 16 illustrates several components of a load plan generator architecture involved for successfully configuring and generating a load plan for a data warehouse in one embodiment according to the present invention.

FIG. 16 is a diagram illustrating load plan generator architecture 1600 in one embodiment according to the present invention. FIG. 16 is merely illustrative of an embodiment or implementation of an invention disclosed herein should not limit the scope of any invention as recited in the claims. One of ordinary skill in the art may recognize through this disclosure and the teachings presented herein other variations, modifications, and/or alternatives to those embodiments or implementations illustrated in the figures.

In this example, FIG. 16 illustrates several components of load plan generator architecture 1600 involved for successfully configuring and generating a load plan for a data warehouse in one embodiment according to the present invention. Set up Configuration Manager User Interface 1610 provides one or more user interfaces for creation of execution plans. In general, an execution plan determines what source system and fact groups are to be loaded by the generated load plan. Configuration Manager Metadata 1620 provides metadata, such as tables that contain data needed by load plan generator 1630 to enable the creation of execution plans to be used by load plan generator 1630.

Load Plan Component 1640 provides a collection of pre-defined load plans containing loading sequence and dependencies for all the different type of source systems and fact groups supported for loading into the data warehouse. ODI 11 g SDK's and API's are utilized to enable load plan generator 1630 to extract information required from load plan components. These SDK's and API's can also then be used as Load Plan Steps 1650 to generate load plan 1670 based on the extracted information and execution plan metadata. Components 1660 are the data stores for fact or aggregate table defined in the ODI data model with flex fields to identify their particular fact group. The data stores for dimension tables need referential constraints defined to fact or aggregate table that refers to them.

Load plan generator 1630 in various embodiments is driven based on the specified source system type, fact groups, and dimension groups related to it. An execution plan specifies what type of source system and fact groups selected by a user. Base on this selection, load plan generator 1630 utilizes the necessary load plan components to generate a single load plan for the specified source system and fact groups. In particular, load plan generator 1630 may determine the General and SDE load plan component based on the source system code selected for the execution plan and substitute the code into the component name to access the proper component for the source system type. The generated load plan will have the necessary level 1 general and SDE component for the selected source system in the execution plan. Each execution plan will generally source from one source system type only. Aside from selecting only the required general and SDE component as indicated in the execution plan configuration table, load plan generator 1630 will also go through selective loading logic and/or any loading options to include only necessary dimension groups and fact group components for loading the selected fact groups for an execution plan.

FIGS. 17A and 17B are screenshots of user interface 1700 configured to allow users to create load plan definitions in one embodiment according to the present invention. Referring to FIG. 17A, in this example, a user is able to select between single or multi-source. The user identifies whether to source from one or more source system by selecting source instances. Load plan generator architecture 1600 allows selection to source from different types of source system. Multi source nodes can be executed in serial or parallel nodes.

Referring to FIG. 17B, in this example, a user is able to select load plan type. Each type is applicable to single source or multi source use cases. Here, a domains only use case is also available. Load plan types as used herein can be defined as follows. Source Extract and Load (SDE, SIL, and PLP) contains all phases and executes warehouse load end to end. Source Extract (SDE) contains general and SDE phase only. This is used, for example, if the extract schedule needs to be staggered because only one SDE may be able to be running at any given point in time. Warehouse Load (SIL and PLP) contains SIL and PLP phase only. This is used, for example, to load from staging to DW tables. Domains Only Extract and Load (SDE and SIL) extracts source domains mapped to a conformed domain. This is needed when a customer maps their source domain members created in the CM domain mapping UI.

Figure 18:
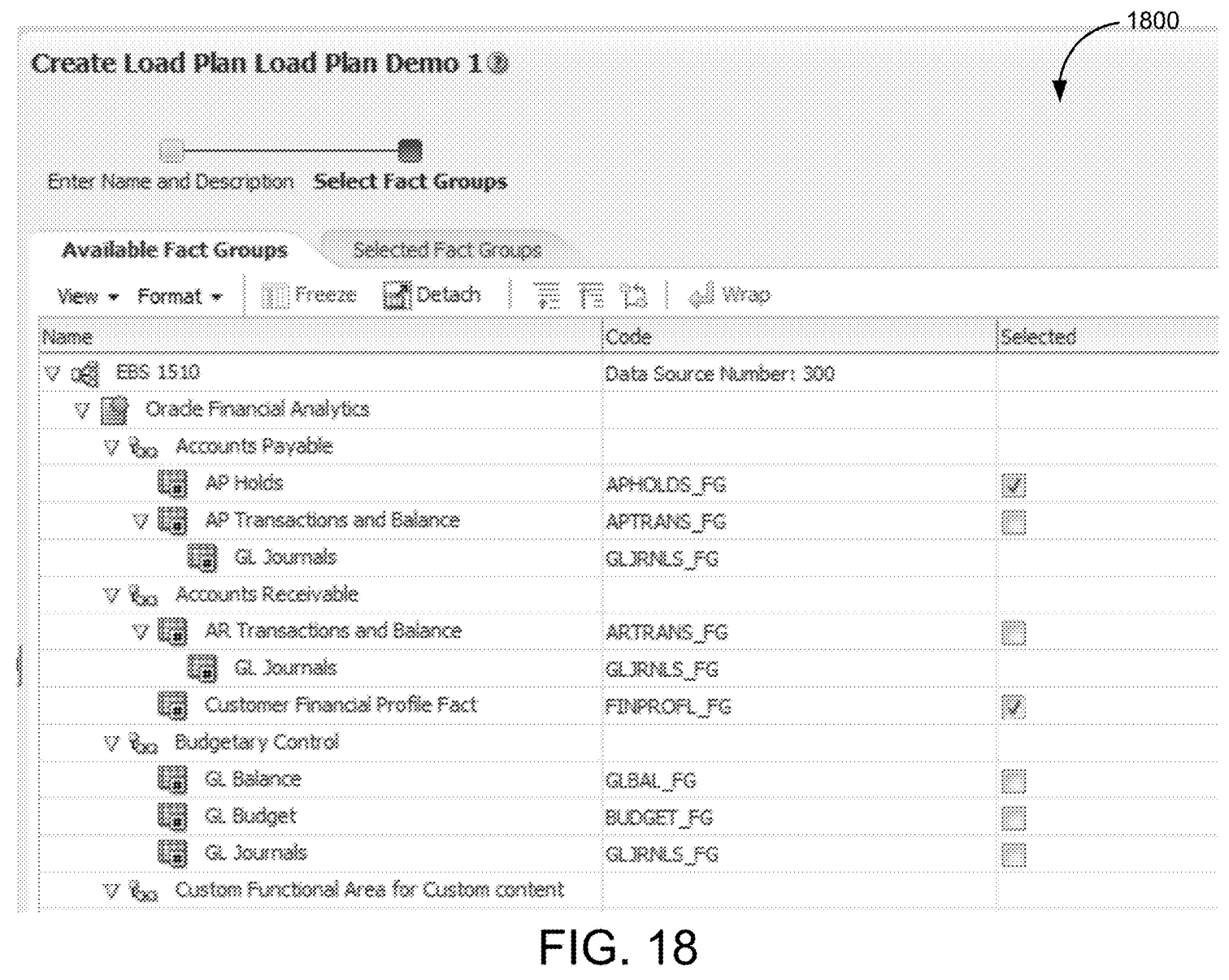

FIG. 18 is a screenshot of user interface 1800 configured to allow users to specify fact groups for load plan definitions. In this example, available fact groups are presented for selection.

Load plan generator architecture 1600 can invoked load plan generation once a load plan definition is created. A load plan definition can be used to regenerate a load plan multiple times. For example, a new load plan may be generated every time and used for different scenarios or as components of another load plan. A load plan definition can be edited and regenerated when the definition is updated.

Figure 19:
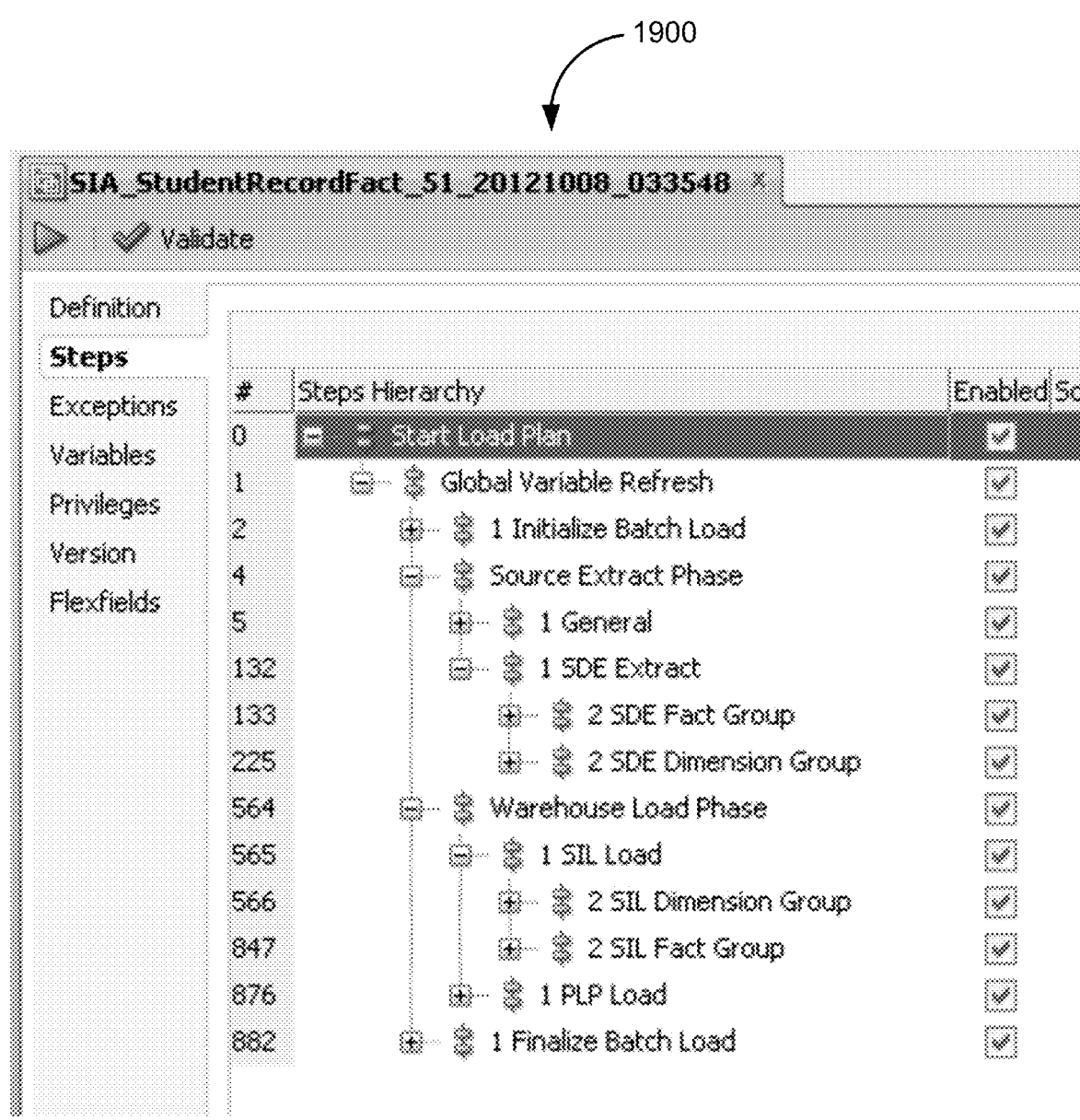
FIG. 19 is a screenshot of a user interface depicting a sample load plan generated according to embodiments of the present invention.
Figure 20:
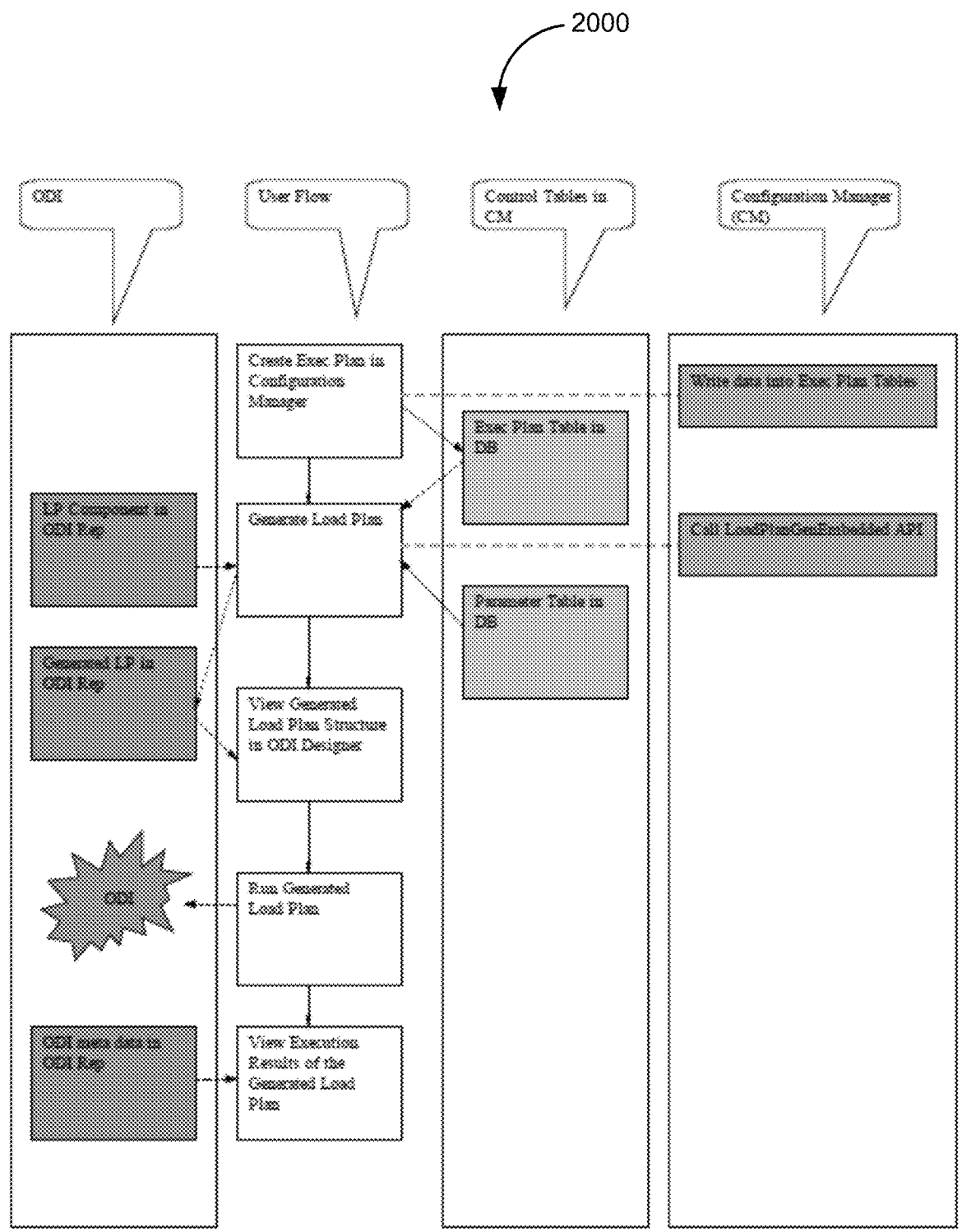
FIG. 20 is a diagram depicting a sequence chart illustrating the interaction of various components of the load plan generator architecture of FIG. 16 in one embodiment according to the present invention.

FIG. 19 is a screenshot of user interface 1900 depicting a sample load plan generated according to embodiments of the present invention. This shows the flow of the phase and group load plan components defined in system components.
Load Plan Generation Rules FIG. 20 is a diagram depicting sequence chart 2000 illustrating the interaction of various components of load plan generator architecture 1600 of FIG. 16 in one embodiment according to the present invention.

In this example, in the user flow, the user creates an execution plan using CM. CM writes the data into one or more tables that can be used by load plan generator 1640 to generate load plan 1670. Load plan generator 1640 generates a load plan utilizing the following metadata. First, fact tables belonging to selected fact groups are determined. Load plan generator 1640 determines the data store and fact group assigned based on the 'OBI Fact/Dimension Group' flex field specified by the user. Load plan generator 1640 also looks to the flex fields defined in ODI topology objects.

Next, Load plan generator 1640 determines the dimensions dependencies to facts. The main source of dependency information is the constraints defined between fact and dimension tables. Dimension to dimension constraint is also supported up to 2 levels.

Next, Load plan generator 1640 determines and readies staging tables related to facts and dimensions Staging and warehouse tables can be resolved via BIAPPS data model naming standards.

Next, Load plan generator 1640 determines related PS or TMP tables used as sources. PS and TMP dependencies are also resolved via scenario information (used as source or lookup) within load plan components for dimension or fact groups.

Finally, Load plan generator 1640 determines keywords in load plan steps for domains and class dimensions Additional resolutions through the use of keywords in load plan steps can be used mainly to resolve steps within class dimensions or domain steps.

Accordingly, load plan generator 1640 figures out which dimension or fact group component to include in the load plan to be generated utilizing:

1. Fact tables belonging to selected fact groups;
2. Dimensions dependencies to Facts;
3. Staging tables related to Facts and Dimensions;
4. Related PS or TMP tables used as source in scenarios; and
5. Keywords in load plan steps for domains and class dimensions.

Multi Source Support

In various aspects, multi-source support is required when loading from more than one transaction source systems. Load plan generator 1640 is able to generate a load plan with multi-source support. There are 3 sequencing options for multi-source:

Extract-Load, Extract-Load, Extract-Load (EL, EL, EL)

In this example, load plan generator 1640 generates separate load plans containing all phases for each source system. Load plan generator 1640 serially executes each to load data into the warehouse.

Extract, Extract, Extract, Load (E,E,E,L)

In this example, load plan generator 1640 generates multiple SDE only (E,E,E) and a SIL/PLP only (L) load plans. Each SDE only load plan will be sourcing from a particular adaptor. The SIL/PLP load plan should be executed after all of the SDE load plans and executed serially of each other to load data into the warehouse.

Extract-Extract-Extract-Load (E-E-E-L)

In this example, load plan generator 1640 generates a single load plan containing multiple SDE phases and one SIL phase. Load plan generator 1640 will simultaneously extract data from different source systems. After SDE completes, the SIL/PLP phase ensues.

Multi-Instance Support

In an environment where multiple instance of the same version of the same adaptor exists (i.e. 2 instances of PSFT 9.0 or 2 instances of EBS 11.5.10), multi-instance support requires a separate model, logical schema, adaptor folder and load plan components per source instance. Load plan generator 1640 implements multiple contexts where the same model, logical schema, adaptor folder and load plan components are used by each instance. Each instance is mapped to a different physical connection via a separate context.

Figure 21:
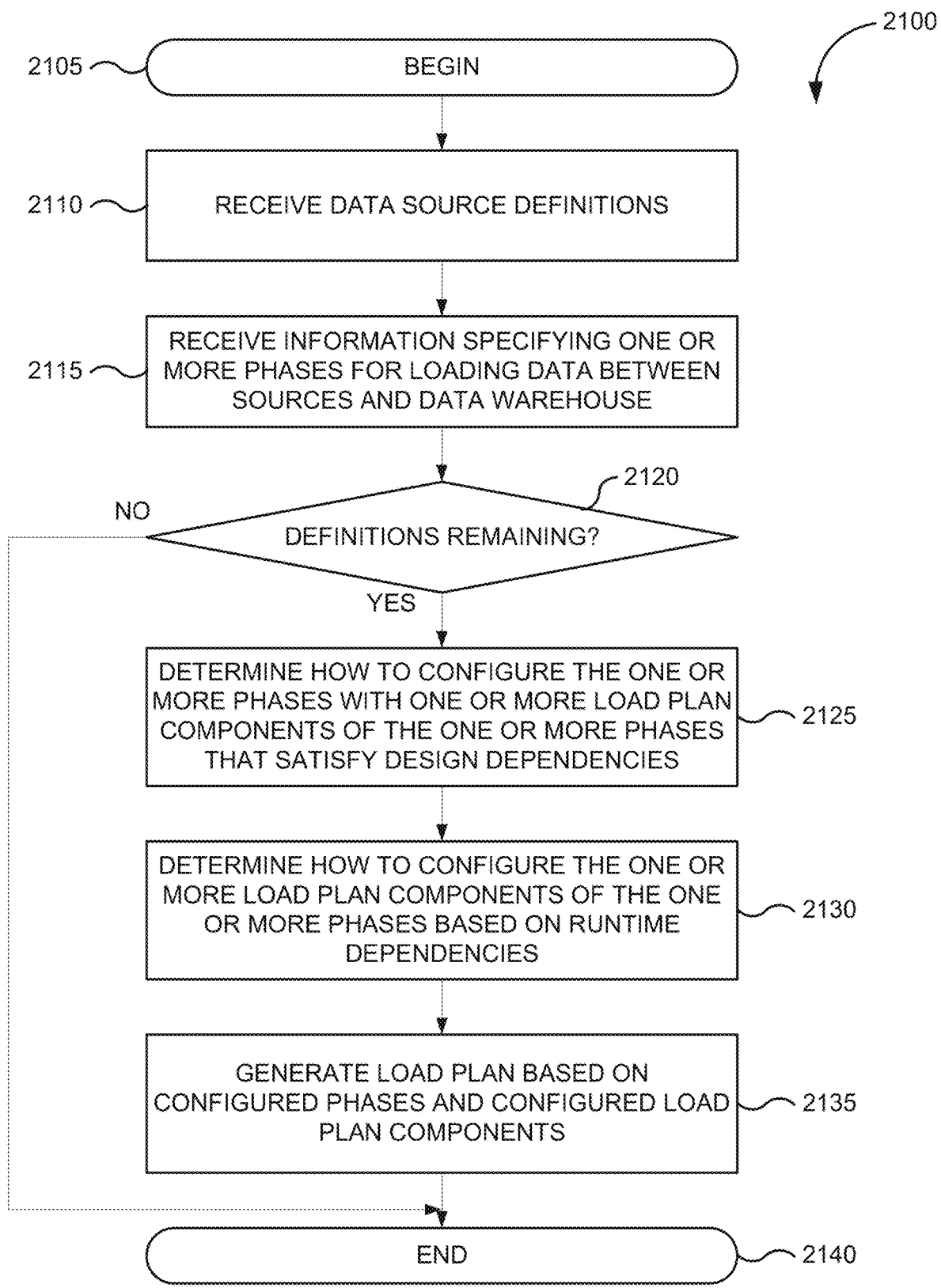
FIG. 21 is a simplified flowchart of a method for load plan generation according to one embodiment of the present invention.

FIG. 21 is a simplified flowchart of method 2100 for load plan generation according to one embodiment of the present invention. Implementations of or processing in the method depicted in FIG. 21 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 2100 of FIG. 21 begins in step 2105.

In step 2110, data source definitions are received. For example, a user defines in CM which the facts and dimensions of one or more sources that are to be used as shown in FIG. 17A. In step 2115, one or more phases are received for loading data between source and data warehouse. The user may define in CM the type of source instances as shown in FIG. 17B. The source definitions and the phases are retrieved by load plan generator 1640 to generate a load plan in step 2120.

In step 2125, a determination is made how to configure the one or more phases with one or more load plan components to satisfy design dependencies. For example, load plan generator 1640 seeds any dimension steps into the ODI repository that never change. In step 2130, a determination is made how to configure the one or more phases with one or more load plan components to satisfy runtime dependencies. For example, load plan generator 1640 associates dimensions to facts, or dimensions or facts to staging tables. As discussed above, load plan generator 1640 may utilize generation rules to resolve design time and runtime dependencies from the metadata.

In step 2135, a load plan is generated based on the configured phases and configured load plan components. FIG. 21 ends in step 2140.

CONCLUSION

Figure 22:
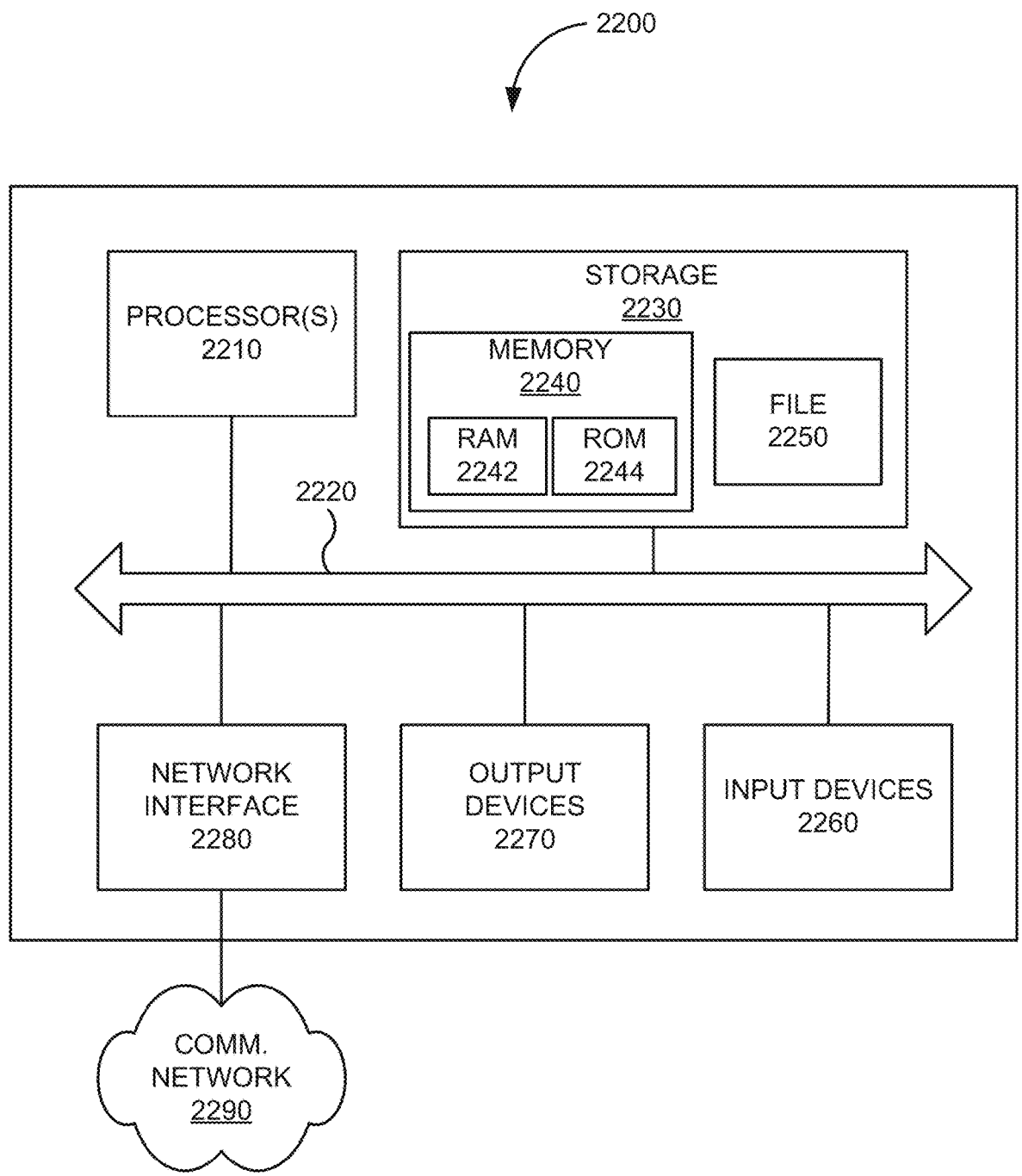
FIG. 22 is a simplified block diagram of a computer system that may be used to practice embodiments of the present invention

FIG. 22 is a simplified block diagram of computer system 2200 that may be used to practice embodiments of the present invention. As shown in FIG. 22, computer system 2200 includes processor 2210 that communicates with a number of peripheral devices via bus subsystem 2220. These peripheral devices may include storage subsystem 2230, comprising memory subsystem 2240 and file storage subsystem 2250, input devices 2260, output devices 2270, and network interface subsystem 2280.

Bus subsystem 2220 provides a mechanism for letting the various components and subsystems of computer system 2200 communicate with each other as intended. Although bus subsystem 2220 is shown schematically as a single bus, alternative embodiments of the bus subsystem may utilize multiple busses.

Storage subsystem 2230 may be configured to store the basic programming and data constructs that provide the functionality of the present invention. Software (code modules or instructions) that provides the functionality of the present invention may be stored in storage subsystem 2230. These software modules or instructions may be executed by processor(s) 2210. Storage subsystem 2230 may also provide a repository for storing data used in accordance with the present invention. Storage subsystem 2230 may comprise memory subsystem 2240 and file/disk storage subsystem 2250.

Memory subsystem 2240 may include a number of memories including a main random access memory (RAM) 2242 for storage of instructions and data during program execution and a read only memory (ROM) 2244 in which fixed instructions are stored. File storage subsystem 2250 provides persistent (non-volatile) storage for program and data files, and may include a hard disk drive, a floppy disk drive along with associated removable media, a Compact Disk Read Only Memory (CD-ROM) drive, a DVD, an optical drive, removable media cartridges, and other like storage media.

Input devices 2260 may include a keyboard, pointing devices such as a mouse, trackball, touchpad, or graphics tablet, a scanner, a barcode scanner, a touchscreen incorporated into the display, audio input devices such as voice recognition systems, microphones, and other types of input devices. In general, use of the term "input device" is intended to include all possible types of devices and mechanisms for inputting information to computer system 2200.

Output devices 2270 may include a display subsystem, a printer, a fax machine, or non-visual displays such as audio output devices, etc. The display subsystem may be a cathode ray tube (CRT), a flat-panel device such as a liquid crystal display (LCD), or a projection device. In general, use of the term "output device" is intended to include all possible types of devices and mechanisms for outputting information from computer system 2200.

Network interface subsystem 2280 provides an interface to other computer systems, devices, and networks, such as communications network 2290. Network interface subsystem 2280 serves as an interface for receiving data from and transmitting data to other systems from computer system 2200. Some examples of communications network 2290 are private networks, public networks, leased lines, the Internet, Ethernet networks, token ring networks, fiber optic networks, and the like.

Computer system 2200 can be of various types including a personal computer, a portable computer, a workstation, a network computer, a mainframe, a kiosk, or any other data processing system. Due to the ever-changing nature of computers and networks, the description of computer system 2200 depicted in FIG. 22 is intended only as a specific example for purposes of illustrating the preferred embodiment of the computer system. Many other configurations having more or fewer components than the system depicted in FIG. 22 are possible.

Although specific embodiments of the invention have been described, various modifications, alterations, alternative constructions, and equivalents are also encompassed within the scope of the invention. The described invention is not restricted to operation within certain specific data processing environments, but is free to operate within a plurality of data processing environments. Additionally, although the present invention has been described using a particular series of transactions and steps, it should be apparent to those skilled in the art that the scope of the present invention is not limited to the described series of transactions and steps.

Further, while the present invention has been described using a particular combination of hardware and software, it should be recognized that other combinations of hardware and software are also within the scope of the present invention. The present invention may be implemented only in hardware, or only in software, or using combinations thereof.

The specification and drawings are, accordingly, to be regarded in an illustrative rather than a restrictive sense. It will, however, be evident that additions, subtractions, deletions, and other modifications and changes may be made thereunto without departing from the broader spirit and scope of the invention as set forth in the claims.

Various embodiments of any of one or more inventions whose teachings may be presented within this disclosure can be implemented in the form of logic in software, firmware, hardware, or a combination thereof. The logic may be stored in or on a machine-accessible memory, a machine-readable article, a tangible computer-readable medium, a computer-readable storage medium, or other computer/machine-readable media as a set of instructions adapted to direct a central processing unit (CPU or processor) of a logic machine to perform a set of steps that may be disclosed in various embodiments of an invention presented within this disclosure. The logic may form part of a software program or computer program product as code modules become operational with a processor of a computer system or an information-processing device when executed to perform a method or process in various embodiments of an invention presented within this disclosure. Based on this disclosure and the teachings provided herein, a person of ordinary skill in the art will appreciate other ways, variations, modifications, alternatives, and/or methods for implementing in software, firmware, hardware, or combinations thereof any of the disclosed operations or functionalities of various embodiments of one or more of the presented inventions.

The disclosed examples, implementations, and various embodiments of any one of those inventions whose teachings may be presented within this disclosure are merely illustrative to convey with reasonable clarity to those skilled in the art the teachings of this disclosure. As these implementations and embodiments may be described with reference to exemplary illustrations or specific figures, various modifications or adaptations of the methods and/or specific structures described can become apparent to those skilled in the art. All such modifications, adaptations, or variations that rely upon this disclosure and these teachings found herein, and through which the teachings have advanced the art, are to be considered within the scope of the one or more inventions whose teachings may be presented within this disclosure. Hence, the present descriptions and drawings should not be considered in a limiting sense, as it is understood that an invention presented within a disclosure is in no way limited to those embodiments specifically illustrated.

Accordingly, the above description and any accompanying drawings, illustrations, and figures are intended to be illustrative but not restrictive. The scope of any invention presented within this disclosure should, therefore, be determined not with simple reference to the above description and those embodiments shown in the figures, but instead should be determined with reference to the pending claims along with their full scope or equivalents.

What is claimed is:

1. A method for generating a load plan used to load data from a data source into a data warehouse, the method comprising:

invoking, by a computer system of a data integration system, a load plan generator, wherein the load plan generator orchestrates loading data from one or more sources into one or more data warehouses to execute a package sequence in a runtime environment and is configured to use metadata stored in a repository of the data integration system, wherein the repository of the metadata is shared by the data integration system and the load plan generator;

receiving, at the computer system, one or more data source definitions each of the one or more data source definitions specifying the data source from which to load data into the data warehouse, a fact group associated with the data source, and a dimension group associated with the data source, wherein the fact group comprises factual information regarding dimensions in the dimension group, and wherein the dimension group comprises dependency information for the factual information in the fact group, and wherein the dimension group represents a hierarchical arrangement of the data; and configuring, with a processor associated with the computer system, for each data source definition in the one or more data source definitions, a phase with a plurality of predefined load plan components based on the data source of the data source definition satisfying one or more design dependencies, wherein each of the plurality of predefined load plan components specifies a task indicative of how data is to be loaded between the data source and the data warehouse, wherein the plurality of predefined load plan components are configured dynamically based on load plan rules, and wherein the plurality of predefined load plan components resolve local dependencies within the fact group or dimension group, and wherein the computer system determines how to load data to the data warehouse based on a type of a load plan component.

2. The method according to claim 1, wherein the load plan comprises a data integrator load plan.

3. The method according to claim 1, wherein the data warehouse comprises an extract, transform, load (ETL)-based data warehouse.

4. The method according to claim 1, wherein loading the load plan comprises a source data extract (SDE) phase, a source independent load (SIL) phase, and a post load process (PLP) phase.

5. The method according to claim 4, wherein the source data extract (SDE) phase comprises extracting data from one or more source systems and loading one or more staging tables.

6. The method according to claim 5, wherein the source independent load (SIL) phase comprises loading the one or more staging tables to one or more dimension tables and/or fact tables.

7. The method according to claim 5, wherein the post load process (PLP) phase comprises loading data into one or more aggregate tables.

8. The method according to claim 1, wherein the load plan corresponds to a subset of fact tables to be populated in the data warehouse.

9. The method according to claim 8, wherein the load plan is an executable object configured to organize a plurality of tasks based on a pre-defined order of the subset of fact tables to be loaded.

10. The method according to claim 1, wherein design time dependencies are addressed separately from run time dependencies.

11. The method according to claim 1, wherein the load plan is stored in a load plan folder in a data integrator repository of the computer system.

12. The method according to claim 1, further comprising displaying, on a user interface, one or more pre-defined load plans comprising a plurality of loading sequences and a plurality of dependencies for a plurality of different types of source systems and fact groups for loading into the data warehouse.

13. A non-transitory computer-readable medium comprising instructions which, when executed by one or more processors of a computer system of a data integration system, causes the one or more processors to generate a load plan used to load data from a data source into a data warehouse, the instructions comprising:

invoke a load plan generator, wherein the load plan generator orchestrates loading data from one or more sources into one or more data warehouses to execute a package sequence in a runtime environment and is configured to use metadata stored in a repository of the data integration system, wherein the repository of the metadata is shared by the data integration system and the load plan generator;

receive one or more data source definitions each specifying the data source from which to load data into the data warehouse, a fact group associated with the data source, and a dimension group associated with the data source, wherein the fact group comprises factual information regarding dimensions in the dimension group, and wherein the dimension group comprises dependency information for the factual information in the fact group, and wherein the dimension group represents a hierarchical arrangement of the data; and configure a phase with a plurality of predefined load plan components based on the data source of the data source definition satisfying one or more design dependencies, wherein each of the plurality of predefined load plan components specifies a task indicative of how data is to be loaded between the data source and the data warehouse, wherein the plurality of predefined load plan components are configured dynamically based on load plan rules, and wherein the plurality of predefined load plan components resolve local dependencies within the fact group or dimension group, and wherein the computer system determines how to load data to the data warehouse based on a type of a load plan component.

14. The computer-readable medium according to claim 13, wherein the load plan is stored in a load plan folder in a data integrator repository of the computer system.

15. The computer-readable medium according to claim 13, wherein the data warehouse comprises an extract, transform, load (ETL)-based data warehouse.

16. The computer-readable medium according to claim 13, wherein loading the load plan comprises a source data extract (SDE) phase, a source independent load (SIL) phase, and a post load process (PLP) phase.

17. A system of a data integration system for generating a load plan used to load data from a data source into a data warehouse, the system comprising:
- one or more processors; and
- a memory storing a set of instructions which when executed by the one or more processors causes the one or more processors to:
- invoke a load plan generator, wherein the load plan generator orchestrates loading data from one or more sources into one or more data warehouses to execute a package sequence in a runtime environment and is configured to use metadata stored in a repository of the data integration system, wherein the repository of the metadata is shared by the data integration system and the load plan generator;
- receive one or more data source definitions each specifying the data source from which to load data into the data warehouse, a fact group associated with the data source, and a dimension group associated with the data source, wherein the fact group comprises factual information regarding dimensions in the dimension group, and wherein the dimension group comprises dependency information for the factual information in the fact group, and wherein the dimension group represents a hierarchical arrangement of the data; and
- configure one or more phases with a plurality of predefined load plan components based on the data source of the data source definition satisfying one or more design dependencies, wherein each of the plurality of predefined load plan components specifies a task indicative of how data is to be loaded between the data source and the data warehouse, wherein the plurality of predefined load plan components are configured dynamically based on load plan rules, and wherein the plurality of predefined load plan components resolve local dependencies within the fact group or dimension group, and
- wherein the system determines how to load data to the data warehouse based on a type of a load plan component.

18. The system according to claim 17, wherein the load plan is stored in a load plan folder in a data integrator repository of the system.

19. The system according to claim 17, wherein the data warehouse comprises an extract, transform, load (ETL)-based data warehouse.

20. The system according to claim 17, wherein loading the load plan comprises a source data extract (SDE) phase, a source independent load (SIL) phase, and a post load process (PLP) phase.

21. The method according to claim 1, wherein the computing system is configured to automate a data integration flow, wherein automation of the data integration flow comprises sequencing an execution of mapping steps or procedure steps in a package and producing a production scenario containing ready-to-use code for each of the mapping steps or the procedure steps.

\* \* \* \* \*

UNITED STATES PATENT AND TRADEMARK OFFICE
CERTIFICATE OF CORRECTION

PATENT NO. : 11,789,964 B2
APPLICATION NO. : 16/238290
DATED : October 17, 2023
INVENTOR(S) : Seng et al.

It is certified that error appears in the above-identified patent and that said Letters Patent is hereby corrected as shown below:

In the Drawings

On sheet 2 of 22, in FIG. 2, under Reference Numeral 216, Line 2, delete "MANAGMENT" and insert -- MANAGEMENT --, therefor.

In the Specification

In Column 4, Line 57, delete "invention" and insert -- invention. --, therefor.

In Column 9, Line 39, delete "maybe" and insert -- may be --, therefor.

In Column 19, Line 18, delete "10g" and insert -- 10 g --, therefor.

In Column 19, Line 19, delete "11g," and insert -- 11 g, --, therefor.

In Column 25, Line 55, delete "(E,E,E,L)" and insert -- (E, E, E, L) --, therefor.

In Column 25, Line 57, delete "(E,E,E)" and insert -- (E, E, E) --, therefor.

Signed and Sealed this
Twenty-fifth Day of June, 2024

Katherine Kelly Vidal
*Director of the United States Patent and Trademark Office*